US011225693B2

(12) United States Patent
Wang et al.

(10) Patent No.: US 11,225,693 B2
(45) Date of Patent: Jan. 18, 2022

(54) COMPOSITIONS AND METHODS FOR IDENTIFYING DRUG RESISTANT TUBERCULOSIS

(71) Applicant: ABBOTT MOLECULAR INC., Des Plaines, IL (US)

(72) Inventors: Hong Wang, Des Plaines, IL (US); Gregor W. Leckie, Des Plaines, IL (US); Vihanga Pahalawatta, Des Plaines, IL (US); Klara Abravaya, Des Plaines, IL (US); Joshua Kostera, Des Plaines, IL (US); Ning Tang, Des Plaines, IL (US); Andrea Frank, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 230 days.

(21) Appl. No.: 16/692,837

(22) Filed: Nov. 22, 2019

(65) Prior Publication Data

US 2020/0080135 A1 Mar. 12, 2020

Related U.S. Application Data

(62) Division of application No. 15/209,453, filed on Jul. 13, 2016, now Pat. No. 10,526,664.

(60) Provisional application No. 62/192,446, filed on Jul. 14, 2015.

(51) Int. Cl.
*C12Q 1/68* (2018.01)
*C12Q 1/689* (2018.01)
*C12N 1/20* (2006.01)
*C12R 1/32* (2006.01)

(52) U.S. Cl.
CPC .............. *C12Q 1/689* (2013.01); *C12N 1/205* (2021.05); *C12Q 2600/106* (2013.01); *C12Q 2600/156* (2013.01); *C12R 2001/32* (2021.05)

(58) Field of Classification Search
CPC ...................................................... C12Q 1/689
See application file for complete search history.

(56) References Cited

U.S. PATENT DOCUMENTS

| 4,948,882 A | 8/1990 | Ruth |
| 5,034,506 A | 7/1991 | Summerton et al. |
| 5,142,047 A | 8/1992 | Summerton et al. |
| 5,185,444 A | 2/1993 | Summerton et al. |
| 5,210,015 A | 5/1993 | Gelfand et al. |
| 5,283,174 A | 2/1994 | Arnold, Jr. et al. |
| 5,370,998 A | 12/1994 | Crawford et al. |
| 5,424,414 A | 6/1995 | Mattingly |
| 5,464,746 A | 11/1995 | Fino |
| 5,491,224 A | 2/1996 | Bittner et al. |
| 5,627,030 A | 5/1997 | Pandian et al. |
| 5,695,934 A | 12/1997 | Brenner |
| 5,714,330 A | 2/1998 | Brenner et al. |
| 5,750,341 A | 5/1998 | Macevicz |
| 5,776,688 A | 7/1998 | Bittner et al. |
| 5,786,149 A | 7/1998 | Leckie et al. |
| 5,912,148 A | 6/1999 | Eggerding |
| 5,925,517 A | 7/1999 | Tyagi et al. |
| 6,103,476 A | 8/2000 | Tyagi et al. |
| 6,130,073 A | 10/2000 | Eggerding |
| 6,150,097 A | 11/2000 | Tyagi et al. |
| 6,210,891 B1 | 4/2001 | Nyren et al. |
| 6,258,568 B1 | 7/2001 | Nyren |
| 6,306,597 B1 | 10/2001 | Macevicz |
| 6,432,360 B1 | 8/2002 | Church |
| 6,485,944 B1 | 11/2002 | Church |
| 6,511,803 B1 | 1/2003 | Church |
| 6,642,000 B1 | 11/2003 | Strizhkov et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,282,337 B1 | 10/2007 | Harris |
| 7,329,492 B2 | 2/2008 | Hardin et al. |
| 7,482,120 B2 | 1/2009 | Buzby et al. |
| 7,501,245 B2 | 3/2009 | Quake et al. |
| 8,143,386 B2 | 3/2012 | Reed et al. |
| 8,703,445 B2 | 4/2014 | Collier et al. |
| 10,072,306 B2 * | 9/2018 | Tang ..................... C12Q 1/689 |

(Continued)

FOREIGN PATENT DOCUMENTS

| CN | 101023170 | 8/2007 |
| CN | 101868542 | 10/2010 |

(Continued)

OTHER PUBLICATIONS

Genbank Accession No. EU884586—*Mycobacterium tuberculosis* strain Iran zabol-163 KatG (katG) gene, partial cds (submitted Jul. 8, 2008, retrieved on Aug. 19, 2021 from http://www.ncbi.nlm.nih.gov/nuccore/EU884586). (Year: 2008).*

Genbank Accession No. M30046—*M. tuberculosis* protein antigen b (Pab) gene, complete cds (submitted Aug. 26, 1994, retrieved on Aug. 19, 2021 from http://www.ncbi.nlm.nih.gov/nuccore/M30046). (Year: 1994).*

Genbank Accession No. CP010332—*Mycobacterium bovis* strain 30, complete genome (submitted Dec. 18, 2014, retrieved on Aug. 19, 2021 from http://www.ncbi.nlm.nih.gov/nuccore/CP010332). (Year: 2014).*

(Continued)

*Primary Examiner* — Teresa E Strzelecka
*Assistant Examiner* — Olayinka A Oyeyemi
(74) *Attorney, Agent, or Firm* — Casimir Jones, S.C.; Kirk Hogan

(57) ABSTRACT

Provided herein are compositions and methods for diagnosing and characterizing tuberculosis infection. In particular, provided herein are compositions and methods for identifying drug resistant tuberculosis.

15 Claims, 21 Drawing Sheets

Specification includes a Sequence Listing.

(56) References Cited

U.S. PATENT DOCUMENTS

| | | | |
|---|---|---|---|
| 10,526,664 B2* | 1/2020 | Wang | C12Q 1/689 |
| 2003/0050470 A1* | 3/2003 | An | C07K 14/82 |
| | | | 536/24.3 |
| 2005/0130173 A1 | 6/2005 | Leamon et al. | |
| 2009/0026082 A1 | 1/2009 | Rothberg et al. | |
| 2009/0035777 A1 | 2/2009 | Kokoris et al. | |
| 2009/0127589 A1 | 5/2009 | Rothberg et al. | |
| 2009/0137406 A1 | 5/2009 | Kinoshita et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0261163 A1* | 10/2010 | Zasedatelev | C12Q 1/689 |
| | | | 435/6.15 |
| 2010/0301398 A1 | 12/2010 | Rothberg et al. | |
| 2013/0095489 A1* | 4/2013 | Posey | C12Q 1/689 |
| | | | 435/6.11 |
| 2013/0240005 A1 | 8/2013 | Kim | |
| 2013/0244887 A1 | 9/2013 | Tam et al. | |
| 2013/0252232 A1 | 9/2013 | Leckie et al. | |
| 2013/0323224 A1 | 12/2013 | Ojha et al. | |
| 2015/0148252 A1 | 5/2015 | Wangh et al. | |
| 2016/0024561 A1* | 1/2016 | Tang | C12Q 1/689 |
| | | | 435/6.12 |
| 2017/0044594 A1* | 2/2017 | Wang | A61P 31/06 |
| 2019/0048400 A1 | 2/2019 | Tang et al. | |

FOREIGN PATENT DOCUMENTS

| | | |
|---|---|---|
| CN | 102618625 A | 8/2012 |
| CN | 103635575 | 3/2014 |
| CN | 103687961 | 3/2014 |
| EP | 2035440 | 3/2009 |
| EP | 2514838 | 10/2012 |
| WO | WO-1992020702 | 11/1992 |
| WO | WO-1995031570 | 11/1995 |
| WO | WO-0018957 A1 | 4/2000 |
| WO | WO-2005012560 | 2/2005 |
| WO | WO-2006084132 A2 | 8/2006 |
| WO | WO-2008127921 | 10/2008 |
| WO | WO-2008140478 | 11/2008 |
| WO | WO-2008152636 | 12/2008 |
| WO | WO-2010132054 | 11/2010 |
| WO | WO-2014139330 | 9/2014 |

OTHER PUBLICATIONS

SantaLucia Jr, John. Physical principles and visual-OMP software for optimal PCR design. PCR Primer Design. Humana Press, 2007: pp. 3-33. (Year: 2007).*
Genbank Accession No. L27989—*Mycobacterium tuberculosis* RNA polymerase beta-subunit (rpoB) gene, complete cds and RNA polymerase beta-subunit rpoC gene, partial cds (submitted Sep. 13, 1994, retrieved on Aug. 19, 2021 from http://www.ncbi.nlm.nih.gov/nuccore/L27989). (Year: 1994).*
Genbank Accession No. X68081—*M.tuberculosis* katG gene for catalase-peroxidase (submitted Jul. 1, 1993, retrieved on Aug. 19, 2021 from http://www.ncbi.nlm.nih.gov/nuccore/X68081). (Year: 1993).*
Genbank Accession No. U66801—Mycobacterium tuberculosis 3-ketoacyl reductase (fabG) gene, complete cds.(submitted Aug. 12, 1996, retrieved on Aug. 19, 2021 from http://www.ncbi.nlm.nih.gov/nuccore/U66801). (Year: 1996).*
Genbank Accession No. AL123456—*Mycobacterium tuberculosis* H37Rv complete genome (submitted Dec. 18, 2012, retrieved on Aug. 19, 2021 from http://www.ncbi.nlm.nih.gov/nuccore/AL123456). (Year: 1998).*
Yam et al., 2013. Rapid identification of mycobacteria and rapid detection of drug resistance in *Mycobacterium tuberculosis* in cultured isolates and in respiratory specimens. Methods in Mol Biol., chapter 12, PCR detection of microbial pathogens,Second Edition, (pp. 171-199). Humana Press, Totowa, NJ. (Year: 2013).*
Genbank Accession No. AF189827—*Mycobacterium* sp. 9502227 direct repeat locus and insertion sequence IS6110 (submitted Sep. 27, 1999, retrieved on Aug. 19, 2021 from http://www.ncbi.nlm.nih.gov/nuccore/AF189827). (Year: 1999).*
Genbank Accession No. AY793000—*Mycobacterium tuberculosis* isolate LH84 DNA-dependent RNA polymerase-beta subunit (rpoB) gene, partial cds (submitted Oct. 26, 2004, retrieved on Aug. 19, 2021 from http://www.ncbi.nlm.nih.gov/nuccore/AY793000). (Year: 2004).*
Genbank Accession No. AY192026—*Mycobacterium tuberculosis* 3-ketoacyl reductase (fabG) gene, fabG-1 allele, partial cds (submitted Dec. 7, 2002, retrieved on Aug. 19, 2021 from http://www.ncbi.nlm.nih.gov/nuccore/AY192026). (Year: 2002).*
Office Action issued in corresponding CN Application No. 2015800494108, dated Feb. 3, 2020, 14 pages.
Lijun, K., et al.., "Clinical value of real-time FQ OCR assay for detection of *Mycobaterium tuberculous/non-tuberculous mycobacteria*" Chinese Journal of Antituberculosis, 2011, vol. 33(5) pp. 263-266_ Abstract.
Office Action issued in corresponding CN Application No. 201680053406.3, dated Jan. 13, 2021, 21 pages.
Adessi C., et al., "Solid Phase DNA Amplification: Characterisation of Primer Attachment and Amplification Mechanisms," Nucleic Acids Research, 2000, vol. 28 (20), pp. E87.
Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.
Bennett S.T., et al., "Toward the 1,000 Dollars Human Genome," Pharmacogenomics, 2005, vol. 6 (4), pp. 373-382.
Birren B., et al., eds., Genome Analysis—A Laboratory Manual, vol. 1, Cold Spring Harbor Laboratory Press, 1997, Table of Contents.
Brenner S., et al., "Gene Expression Analysis by Massively Parallel Signature Sequencing (MPSS) on Microbead Arrays," Nature Biotechnology, 2000, vol. 18 (6), pp. 630-634.
Co-pending U.S. Appl. No. 11/671,956, filed Feb. 6, 2007.
Co-pending U.S. Appl. No. 11/781,166, filed Jul. 20, 2007.
International Search Report and Written Opinion for Application No. PCT/US2016/042108, dated Oct. 28, 2016, 17 pages.
MacLean D., et al., "Application of 'next-generation' Sequencing Technologies to Microbial Genetics," Nature Reviews Microbiology, 2009, vol. 7 (4), pp. 287-296.
Margulies M., et al., "Genome Sequencing in Microfabricated High-Density Picolitre Reactors," Nature, 2005, vol. 437 (7057), pp. 376-380.
Massire C., et al., "Simultaneous Identification of Mycobacterial Isolates to the Species Level and Determination of *Tuberculosis* Drug Resistance by PCR followed by Electrospray Ionization Mass Spectrometry," Journal of Clinical Microbiology, 2010, vol. 49 (3), pp. 908-917.
Mitra R.D., et al., "Fluorescent in Situ Sequencing on Polymerase Colonies," Analytical Biochemistry, 2003, vol. 320 (1), pp. 55-65.
Morozova O., et al., "Applications of Next-generation Sequencing Technologies in Functional Genomics," Genomics, 2008, vol. 92 (5), pp. 255-264.
Morrison, L.E. et al., "Labeling Fluorescence In Situ Hybridization Probes for Genomic Targets," Methods in Molecular Biology, 2002, vol. 204, pp. 21-40.
Nelson N.C., et al., "Detection of Acridinium Esters by Chemiluminescence," in: Nonisotopic Probing, Blotting and Sequencing, 1995, Chapter 17, Academic Press, Inc., pp. 391-428.
Pennisi E., "Genomics. Semiconductors Inspire New Sequencing Technologies," Science, 2010, vol. 327 (5970), p. 1190.
Shendure J., et al., "Accurate Multiplex Polony Sequencing of an Evolved Bacterial Genome," Science, 2005, vol. 309 (5741), pp. 1728-1732.
Voelkerding K.V., et al., "Next-Generation Sequencing: from Basic Research to Diagnostics," Clinical Chemistry, 2009, vol. 55 (4), pp. 641-658.
Abate D., et al., "Isoniazid and rifampicin resistance mutations and their effect on second-line anti-tuberculosis treatment.", The International Journal of *Tuberculosis* and Lung Disease:The Official

(56) References Cited

OTHER PUBLICATIONS

Journal of The International Union Against Tuberculosis and Lung Disease, Aug. 2014, vol. 18, No. 8, pp. 946-951.

N'guessan K., et al., "Assesment of the genotype MTBDRplus assay for rifampin and iosniazied resisitance detetection on sputum samples in Cote d'Ivoire." European Journal of Microbiology & Immunology, Sep. 2014, vol. 4, No. 3 pp. 166-173.

Nosova E Yu, et al., "Comparative analysis of TB-Biochip, Xpert MTB/RIF, and GenoType MTBDRplus test systems for rapid determination of mutations responsible for drug resistance of *M-tuberculosis* complex (in sputum from patients in Moscow region)", Molecular Biology (Moscow), vol. 47, No. 2, Mar. 2013, pp. 236-241.

Tang Ning, et al., "Analytical and clinical performance of Abbott RealTime MTB, an assay for detection of *Mycobacterium tuberculosis* in pulmonary specimens", Tuberculosis (Amsterdam), vol. 95, No. 5, Sep. 2015, pp. 613-619.

Singhal, Ritu, et al., "Detection of multi-drug resistance & characterization of muations in *Mycobacterium tuberculosis* isolates from North-eastern states of India using GenoTyle MTBDRplus assay", Indidan Journal of Medical Research, vol. 140, Oct. 2014, pp. 501-506.

Supplementary EP Search Report issued in corresponding EP Application No. 16825119.7, dated Dec. 3, 2018, 10 pages.

Andersen A.B., et al., "Structure and Mapping of Antigenic Domains of Protein Antigen B, A 38,000-molecular-weight Protein of *Mycobacterium tuberculosis*," Infection and Immunity, 1989, vol. 57 (8), pp. 2481-2488.

Banada P.P., et al., "Containment of Bioaerosol Infection Risk by the Xpert Mtb/rif Assay and its Applicability to Point-of-care Settings," Journal of Clinical Microbiology, 2010, vol. 48 (10), pp. 3551-3557.

Gilpin C.M., et al., "Failure of Commercial Ligase Chain Reaction to Detect *Mycobacterium tuberculosis* Dna in Sputum Samples from a Patient with Smear-positive Pulmonary *Tuberculosis* Due to a Deletion of the Target Region," Journal of Clinical Microbiology, 2002, vol. 40 (6), pp. 2305-2307.

Martin.P., et al, "Ein Neuer Zugang Zu 2'-0-Alkylribonucleosiden Und Eigenschaften Deren Oligonculeotide," Helvetica Chimica Acta , 1995, vol. 78, pp. 486-504.

Mathema B., et al., "Molecular Epidemiology of *Tuberculosis*: Current Insights," Clinical Microbiology Reviews, 2006, vol. 19 (4), pp. 658-685.

Nielsen P.E., et al., "Sequence-selective Recognition of DNA by Strand Displacement with a Thymine-substituted Polyamide," Science, 1991, vol. 254 (5037), pp. 1497-1500.

Thierry D., et al., "Is6110, an Is-like Element of *Mycobacterium tuberculosis* Complex," Nucleic Acids Research, 1990, vol. 18 (1), p. 188.

Tortoli E.P., et al., "Use of Bactec Mgit 960 for Recovery of *Mycobacteria* from Clinical Specimens: Multicenter Study," Journal of Clinical Microbiology, 1999, vol. 37 (11), pp. 3578-3582.

Wallis R.S., et al., "Drug Tolerance in *Mycobacterium tuberculosis*," Antimicrobial Agents and Chemotherapy, 1999, vol. 43 (11), pp. 2600-2606.

Warren R.M., et al., "Differentiation of *Mycobacterium tuberculosis* Complex by Pcr Amplification of Genomic Regions of Difference," The International Journal of *Tuberculosis* and lung Disease, 2006, vol. 10 (7), pp. 818-822.

International Search Report and Written Opinion for Application No. PCT/US2015/039362, dated Nov. 30, 2015, 18 pages.

Kusum et al., "Multiplex PCR for rapid diagnosis of *tuberculous* meningitis." J Neurol. Oct. 2011;258(10):1781-7.

Leung et al., "Rapid and simultaneous detection of *Mycobacterium tuberculosis* complex and Beijing/W genotype in sputum by an optimized DNA extraction protocol and a novel multiplex real-time PCR." J Clin Microbiol. Jul. 2011;49(7):2509-15. Retrieved from the Internet:URL:http:fjjcm.asm.orgjcontent/49/7/2509, Abstract Only.

Savelkoul et al., "Detection of *Mycobacterium tuberculosis* complex with Real Time PCR: comparison of different primer-probe sets based on the IS6110 element." J Microbiol Methods. Jul. 2006;66(1):177-80.

Sharma et al., "Evaluation of multiplex polymerase chain reaction utilising multiple targets in *Mycobacterium tuberculosis* direct test negative but culture positive cases: a potential method for enhancing the diagnosis of *tuberculosis*." Indian J Med Microbiol. Oct. 2013-Dec.;31(4):370-3.

Search Report of EP 15824241.2, dated Nov. 20, 2017, 10 pages.

Ashkin, et al., Indian Journal of Medical Microbiology, vol. 31, No. 4, Oct.-Dec. 2013, pp. 370-373.

Sharma, et al.,"Novel multi-targeted polymerase chain reaction for diagnosis of presumed tubercular uveitis", Journal of Ophthalmic Inflammation and Infection, 3 (2013), 25, pp. 1-7.

Japanese Office Action, JP Patent Application No. 2017-503844, dated May 28, 2019, 14 pages.

Chen, et al., "Performance of the new automated Abbott RealTime MTB assay for rapid detection of *Mycobacterium tuberculosis* complex in respiratory specimens", EJCM and Infectious Diseases, 2015, vol. 34, No. 9, pp. 1827-1832.

Search Report of EP 16825119.7, dated Nov. 19, 2019, 8 pages.

\* cited by examiner

FIG. 3A  FIG. 3B  FIG. 3C  FIG. 3D  FIG. 3E

Rxn A (RIF-1): CFR610(Rox) Pb1  NED Pb2  VIC Pb3  FAM Pb4  Quasar670(Cy5) IC-A rpoB

FIG. 3F  FIG. 3G  FIG. 3H  FIG. 3I  FIG. 3J

Rxn B (RIF-2): CFR610(Rox) Pb5  NED Pb6  VIC Pb7  FAM Pb8  Quasar670(Cy5) IC-B rpoB

FIG. 3K  FIG. 3L  FIG. 3M  FIG. 3N  FIG. 3O

Rxn C (INH): CFR610(Rox) inhA wt  NED katG wt  VIC inhA -15T  FAM katG 315T1  Quasar670(Cy5) IC-C katG
inhA
Promoter

FIG. 3P

| Sample ID | Well | Row | Column | ROX Ct | ROX MR | NED Ct | NED MR | VIC Ct | VIC MR | FAM Ct | FAM MR | CY5 Ct | CY5 MR | Results | Interpretation |
|---|---|---|---|---|---|---|---|---|---|---|---|---|---|---|---|
| S2 | B2 | G | 10 | 22.31 | 0.228 | 21.64 | 0.249 | 20.89 | 0.244 | 21.62 | 0.239 | 29.68 | 0.329 | rpoB wt | RIF R- |
|  | B3 | G | 11 | 22.17 | 0.285 | 21 | 0.252 | 21.33 | 0.3 | 22.32 | 0.238 | 28.81 | 0.331 |  |  |
|  | B4 | G | 12 | 18.9 | 0.283 | 19.35 | 0.238 | -1 | 0.072 | -1 | 0.053 | 29.41 | 0.296 | katG wt, inhA wt | INH R- |

FIG. 3Q   FIG. 3R   FIG. 3S   FIG. 3T   FIG. 3U
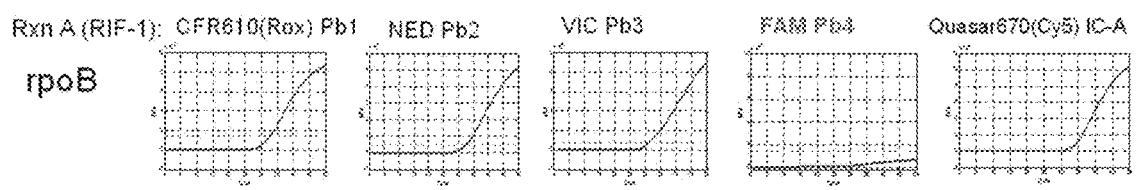
FIG. 3V   FIG. 3W   FIG. 3X   FIG. 3Y   FIG. 3Z
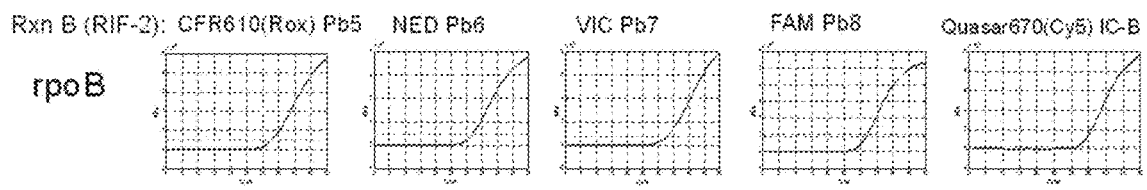
FIG. 3AA   FIG. 3AB   FIG. 3AC   FIG. 3AD   FIG. 3AE
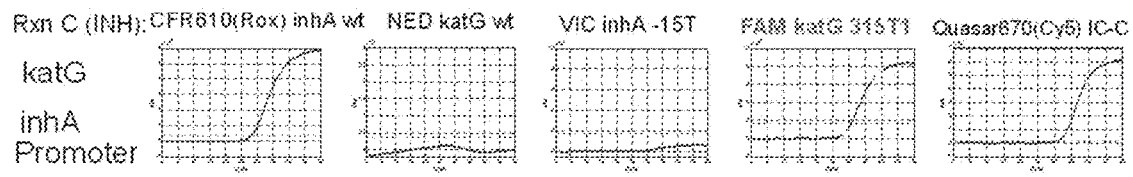
FIG. 3AF

T
1681
GAGGTGGAGTACGTGCCCTCGTCTGAGGTGGACTACATGGACGTCTCGCCCCGCCAGATGGTGTCGGTGGCCACCGCGATGAT
TCCCTTCCTGGAGCACGACGACGCCAACCGTGCCCTC       SEQ ID NO. 33

E673D
1801
ATGGGGGCAAACATGCAGCGCCAGGCGGTGCCGCTGGTCCGTAGCGAGGCCCCGCTGGTGGGCACCGGGATGGAGCTGCGCGC
GGCGATCGACGCCGGCGACGTCGTCGTCGCCGAAGAA       SEQ ID NO. 34

1921
AGCGGCGTCATCGAGGAGGTGTCGGCCGACTACATCACTGTGATGCACGACAACGGCACCCGGCGTACCTACCGGATGCGCAA
GTTTGCCCGGTCCAACCACGGCACTTGCGCCAACCAG       SEQ ID NO. 35

2041
TGCCCCATCGTGGACGCGGGCGACCGAGTCGAGGCCGGTCAGGTGATCGCCGACGGTCCCTGTACTGACGACGGCGAGATGGC
GCTGGGCAAGAACCTGCTGGTGGCCATCATGCCGTGG       SEQ ID NO. 36

2161
GAGGGCCACAACTACGAGGACGCGATCATCCTGTCCAACCGCCTGGTCGAAGAGGACGTGCTCACCTCGATCCACATCGAGGA
GCATGAGATCGATGCTCGCGACACCAAGCTGGGTGCG       SEQ ID NO. 37

2281
GAGGAGATCACCCGCGACATCCCGAACATCTCCGACGAGGTGCTCGCCGACCTGGATGAGCGGGGCATCGTGCGCATCGGTGC
CGAGGTTCGCGACGGGGACATCCTGGTCGGCAAGGTC       SEQ ID NO. 38

2401
ACCCCGAAGGGTGAGACCGAGCTGACGCCGGAGGAGCGGCTGCTGCGTGCCATCTTCGGTGAGAAGGCCCGCGAGGTGCGCGA
CACTTCGCTGAAGGTGCCGCACGGCGAATCCGGCAAG       SEQ ID NO. 39

2521
GTGATCGGCATTCGGGTGTTTTCCCGCGAGGACGAGGACGAGTTGCCGGCCGGTGTCAACGAGCTGGTGCGTGTGTATGTGGC
TCAGAAACGCAAGATCTCCGACGGTGACAAGCTGGCC       SEQ ID NO. 40

2641
GGCCGGCACGGCAACAAGGGCGTGATCGGCAAGATCCTGCCGGTTGAGGACATGCCGTTCCTTGCCGACGGCACCCCGGTGGA
CATTATTTTGAACACCCACGGCGTGCCGCGACGGATG       SEQ ID NO. 41

2761
AACATCGGCCAGATTTTGGAGACCCACCTGGGTTGGTGTGCCCACAGCGGCTGGAAGGTCGACGCCGCCAAGGGGGTTCCGGA
CTGGGCCGCCAGGCTGCCCGACGAACTGCTCGAGGCG       SEQ ID NO. 42

2881
CAGCCGAACGCCATTGTGTCGACGCCGGTGTTCGACGGCGCCCAGGAGGCCGAGCTGCAGGGCCTGTTGTCGTGCACGCTGCC
CAACCGCGACGGTGACGTGCTGGTCGACGCCGACGGC       SEQ ID NO. 43

3001
AAGGCCATGCTCTTCGACGGGCGCAGCGGCGAGCCGTTCCCGTACCCGGTCACGGTTGGCTACATGTACATCATGAAGCTGCA
CCACCTGGTGGACGACAAGATCCACGCCCGCTCCACC       SEQ ID NO. 44

3121
GGGCCGTACTCGATGATCACCCAGCAGCCGCTGGGCGGTAAGGCGCAGTTCGGTGGCCAGCGGTTCGGGGAGATGGAGTGCTG
GGCCATGCAGGCCTACGGTGCTGCCTACACCCTGCAG       SEQ ID NO. 45

3241
GAGCTGTTGACCATCAAGTCCGATGACACCGTCGGCCGCGTCAAGGTGTACGAGGCGATCGTCAAGGGTGAGAACATCCCGGA
GCCGGGCATCCCCGAGTCGTTCAAGGTGCTGCTCAAA       SEQ ID NO. 46
```

3361
GAACTGCAGTCGCTGTGCCTCAACGTCGAGGTGCTATCGAGTGACGGTGCGGCGATCGAACTGCGGAAGTGACGACGAGGA
CCTGGAGCCGGGCCCGCCAACCTGGGAATCAATCTG   SEQ ID NO. 47

3481 TCCCGCAACGAATCGCAAGTGTCGAGGATCTTGCGTAA
SEQ ID NO. 48

FIG. 4B rpoB F1206 to R1398 193 bp amplicon sequence vs NCBI nucleotide database
blast result: nt mutation identification

[>Rv0667nt-H37Rv (Mycobacterium tuberculosis H37Rv (GB:AL123456): rpoB nt 1206-1398
that includes the 81 bp rpoB
(nt 1276-1356; 27 aa from G507 to L533) rifampicin resistance-determining
region (RRDR)]

```
                 L511

EF628323.1 Mtb Belarus-414 Minsk(RIF-R) (CAG to GAG,
Q510E) G
EF628316.1 Mtb Belarus-139(RIF-R)
(GAC to GTC, D516V) T
EF628310.1 Mtb Belarus-414(RIF-R) (CAG to GAG,
Q510E) G
EQ985221.1 Mtb 1599 (CTG to CCG, L511P; GAC to GGC,
D516G) C G

FIG. 4E

```
                       L511  Q513      D516
              V E A I T P Q T L I N I R P V V A A I K E F F
T S Q L S Q F M D Q N N P L
1206
CGTGAGGCGATCACACCGCAGACGTTGATCAACATCCGGCCGGTGGTCGCCGCGATCAAGGAGTTCTTCACCCAGCTGAGC
CAGTTCATGGACCAGAACAACCCGC SEQ ID NO. 52
```
DQ985220.1 Mtb 30                            (CTG to CCG, L511P; GAC to TAC, D516Y)
AY308005.1 Mtb 3018P(MDR)                    (CTG to CCG, L511P; CAA to CGA, Q513R)
AY271375.1 Mtb 274P(MDR) (GAC to GTC, D516V)
AY271367.1 Mtb 1608P(MDR) (GAC to GTC, D516V)
AY271366.1 Mtb 1536P(MDR)                    (CTG to CCG, L511P; CAA to CGA, Q513R)
AJ318819.1 Mtb 1417-97(RIF-R)                (CTG to CCG, L511P; GAC to GGC, D516G)
AJ318818.1 Mtb 1415-97(RIF-R)                (CTG to CCG, L511P; GAC to GGC, D516G)
AJ318817.1 Mtb 2348-98(RIF-R)                (CTG to CCG, L511P; GAC to GGC, D516G)
(CAG to CGG, Q490R) G     AJ318815.1 Mtb 2540-97(RIF-R)
AY823318.1 Mtb MDRW64(MDR)                                          (CAA to CCG, Q513P)
AY823311.1 Mtb MDR119(MDR)                               (GAC to TAC, D516Y; CAG to CCG, Q517P)
JN315354.1 Mtb pk_P_3-1(RIF-R)              (GCC ins between S512 and Q513)
DQ250581.1 Mtb ZY086(RIF-R)     (AGC to AGG, S509S; CTG to CCG, L511P; GAC to GTC, D516V)
EF628336.1 Mtb Belarus-23623 Brest(RIF-R)                           (CAG to GAG, Q510E)
EF628317.1 Mtb MDR-Belarus-94(RIF-R)(GGC to AGC, G507S; CAG to AAG, Q510K)
    (TTG to TYTG in L492)    EF628235.1 Mtb MDR-Belarus-447-Minsk(RIF-R)
AY308010.1 Mtb 3534P(MDR) (GAC to GTC, D516V)
AJ318821.1 Mtb 1071-983(RIF-R)     (GTG to GCG, V498A) C
        (GAC to GTC, D516V)
AY823315.1 Mtb 3MDRW41(MDR)
        (GAC to GAG, D516E)
AY823314.1 Mtb MDR24(MDR)                                           (ACC to ATC, T508I)
AY823313.1 Mtb MDR137(MDR) (GAC to GCC, D516A)
AY823316.1 Mtb MDR97(RIF-R) (ATG to GTG, M515V)
EF628359.1 Mtb Iran-103 Zabol(RIF-R)         (GAG to AAG, E504K) A
EF628309.1 Mtb MDR-Belarus-468(RIF-R)                    (CAG to GAG, Q510E) G (CCG-CCC, P520P; CTG-TTG, L521L)
AY663788.1 Mtb G351(RIF-R)                                          (CAA to GAA, Q513E)
AJ318916.1 Mtb 1255-98(MDR) (TTC to TTT, F514F)
EF628342.1 Mtb Iran-3708(RIF-R)    (GTG to ATG, V498M) A (AGC to AG- in S509)
EF628340.1 Mtb MDR-Iran-163(RIF-R)(GTG to ATG, V498M) A (AGC to AG- in S509)
EF628339.1 Mtb Iran-441(RIF-R)     (GTG to ATG, V498M) A (AGC to AG- in S509)
AY280822.1 Mtb 2916P(MDR) (GAC to GTC, D516V)
EF628347.1 Mtb Iran-290(MDR)                                        (ACC to CCC, T508P)
EF628333.1 Mtb MDR-Belarus-3255 Brest(RIF-R)(GGC to AGC, G507S; CAG to AAG, Q510K)
                (CCG to CCC, P520P)
EF628332.1 Mtb MDR-Belarus-2262 Brest(RIF-R)             (CAG to GAG, Q510E)

FIG. 4F

EF628330.1 Mtb MDR-Belarus-2715 Brest(RIF-R)　　(CAG to TAG, Q510end; GAC to GTC, D516V)
EF628331.1 Mtb MDR-Belarus-407(RIF-R)
　　(GAC to GTC, D516V)
EF628308.1 Mtb MDR-Belarus-402(RIF-R)　　(GGC to GCC, G507A; AGC to GGC, S512G)
EF628307.1 Mtb MDR-Belarus-412(RIF-R)　　(ACC to CCC, T508P; AGC to GGC, S512G)
AJ318813.1 Mtb 1763-97(RIF-R)　　　　　　　　　　　　　　　　　(ATTCAT ins between S513 and Q515)
EF628332.1 Mtb 633 Tehran(RIF-R)
　　(CAG to -AG at Q510)

L511　Q513　　D516
　　　　V　E　A　I　T　P　Q　T　L　I　N　I　R　P　V　V　A　A　I　K　E　F　F
T　S　Q　L　S　Q　F　M　D　Q　N　N　P　L
1206
CGTGGAGGCGATCACACCGCAGACGTTGATCAACATCCGGCCGGTGGTCGCCGCGATCAAGGAGTTCTTC　　CAG　　AGC
　GAGC　ATTCAT　　C　AGAACAACCCGC　　SEQ ID NO. 52
JN819066.1 Mtb 2001-1669 mutant1
　　(AAC to AAA, N519K)
HQ844250.1 Mtb pan-DR-TB1(DR)
　　(GAC to GGC, D516G)
EF628354.1 Mtb 19 Kerman(RIF-R)　　　　　　　　　　　　　　　　(GGC to GGT, G507G)
　　　　　　　　　　(AAC to ATC, N494I) T　　　EF628346.1 Mtb Iran-29 Tehran(RIF-R)
EF628331.1 Mtb MDR-Belarus-85 vitebsk(RIF-R)　　　　　　　　(CAG to TAG, Q510end)
EF628326.1 Mtb MDR-Belarus-894 vitebsk(RIF-R)　　　　　　　(CAG to AAG, Q510K)
EF628335.1 Mtb MDR-Belarus-507 Magilev(RIF-R)　　　　　　　(CAG to GAG, Q510E)
EF628322.1 Mtb MDR-Belarus-443 Minsk(RIF-R)　　　　　　　　(CAG to GAG, Q510E)
EF628321.1 Mtb MDR-443-Minsk(RIF-R)　　　　　　　　　　　　(CAG to GAG, Q510E)
EF628319.1 Mtb MDR-85-vitebsk(RIF-R)　　　　　　　　　　　(CAG to GAG, Q510E)
EF628301.1 Mtb MDR-Belarus-443 (RIF-R)　　　　　　　　　　(CAG to GAG, Q510E)
　　　　　　　　　　　　　(GTG to ATG, V498M) A　　(CAG to -AG, Q510)　EF628358.1 Mtb MDR-Iran-98/1384(RIF-R)
EF628350.1 Mtb Iran-1757 PII(RIF-R)　　　　　　　　　　　(GGC to CGC, G507R)
EF628369.1 Mtb Iran-33 PII(RIF-R) (GGC to GAT, G507D)
EF628361.1 Mtb Iran-165 Zabol(RIF-R)　　　　　　　　　　　　　　　　(CTG to CCG, L511P)
EF628343.1 Mtb Iran-3458(RIF-R)　(GTG to ATG, V498M) A
　(ACC to CCC, T508P)
EF628320.1 Mtb Belarus-455 Minsk(RIF-R)　　　　　　　　　　(ACC to ACG, T508T)　　(CAG to GAG, Q510E)
EF628367.1 Mtb MDR-Iran-303-281 Mashad(RIF-R)　　　　　　　(CTG to CCG, L511P)　(CCG to C-G, P520-)
EF628344.1 Mtb MDR-Iran-36 asli Iran(RIF-R)
(GCCAATT to CCAATTT between S512 to F514)
EF628364.1 Mtb Iran-3542(RIF-R)　(GTG to ATG, V498M) A　(GAG-AAG,E504K)A　　(CAC to TCA, between G507 and T508)
EF628303.1 Mtb MDR-Belarus-571(RIF-R)　　　　　　　　　　(ACC to ACG, T508T)　　(CAG to GAG, Q510E)
　　　EF628302.1 Mtb MDR-Belarus-453(RIF-R)　　　　　　　　(TTC to TGC, F506C)
HQ997366.1 Mtb Seq190795　　　　　　　　　　　　　　　　　　(CTG to CCG, L511P)　　(ATG to CTG, M515L)
EF628296.1 Mtb MDR-Belarus-4(RIF-R)　　　　　　　　　　　(ACC to ACG, T508T)　　(CAG to SAG, Q510-)
DQ205140.1 Mtb TBM554(RIF-R)
(GAC to GCC, D516A)
AY232115.1 Mtb(RIF-R)
(GAC to GGC, D516G)

FIG. 4G

HQ997368.1 Mtb Seq209853
                    (XXX ins at N518)
EF628363 Mtb Iran-173 Zabol(RIF-R)                    T        A (GTC to
TTC,V499F; GAG to AAG,E504K; CAG to -AG,Q510-)
JN819069.1 Mtb 2002-1640
            (ATG to AAATTCATG ins at M515)
EF628365 Mtb MDR-Iran-159(RIF-R)(GGC-GGT,G507G;AGC to ACC,S512T;CAA to
TAA,Q513end)
DQ205439 Mtb TBM552(RIF-R)
          (GAC to GGC, D516G)
AY823313.1 Mtb MDR11(MDR)
        (GCTGAGCCAA to A del between Q510 and Q513)
            (CAG to CAT, Q490H)   AF515787.1 Mtb TB 2(RIF-R)
AF360399 Mtb F15(RIF-R)                             (CTG to CCG, L511P; AGC to
ACC,S512T)
                                T   C   A    T        A
(GAG-AAG,E504K;GGC-AGT,G507S) EF628355.1
       (AAC-TAC,N494Y;CCG-CCC,P497P;GTG-ATG,V498M;GTC-TTC,V499F)
Mtb 10-2 Tehran(RIF-R)
EF628341 Mtb Iran-163 Tehran(RIF-R)                 A           A  S (GTG-ATG,V498M;GAG-AAG,E504K;TTC-TGC,F505C;GGC-GGT,G507G;ACC-CCC,T508P;AGC-
TGC,S509C;CAA-CAG,Q513Q;TTC-TAC,F514Y,CAG-CTG,Q517L)
              L511   Q513      D516
              V  E  A  I  T  P  Q  T  L  I  N  I  R  P  V  V  A  I  K  E  F  F
T  S  Q  L  S  Q  F  M  Q  N  N  P  L
1206
CTXGAGGCGATCACACCGCAGACGTTGATCAACATCCGGCCGGTGGTCGCCGCGATCAAGGAGTTCTTCXXXCAGXAGC
XGAGCXATTCATXGXCXAGAACAACCGCXX SEQ ID NO. 52
EF628314 Mtb C                        TC   T          C        G              C (GAG-CAG,E485Q;ACG-ACT,T491T;TTG-CTG,L492L;AAC-TAC,N494Y;GTC-CTC,V499L;AAG-
AGG,K503R;GGC-GCC,G507A;AGC-GGC,S512G;CCG-CCC,P520P)
AY271363.1 Mtb 1077P(MDR)
(GAC to GTC, D516V)
AF055893 Mtb F7(MDR)   (CTG to CCG, L511P; AGC to ACC,S512T; GAC to GTC, D516V)

EF628362 Mtb MDR-Iran-600 Tehran(RIF-R)
(AGC to GAC, S509D; CTG to GTG, L511V; CAA to GAA, Q513E; AAC to AAG, N519K)
EF628361 Mtb MDR-Iran-663 kerman(RIF-R)
(AGC to GAC, S509D; CTG to GTG, L511V; CAA to GAA, Q513E; AAC to AAG, N519K)
   915181 Mtb 331102070021
  (CTG to CCG, L511P)
  HM776956.1 Mtb tb15
  (CTG to CCG, L511P)
  HM776946.1 Mtb tb01
  (CTG to CCG, L511P)
  HM776947.1 Mtb tb02                                    (AAG to -AG, K503-)
JQ425738.1 Mtb 197(MDR)
(XXX ins between S512 and Q513)
HM776957.1 Mtb tb31                                     (AAG to -AG, K503-)
(CAA to C-A, Q513-)
  HM776952.1 Mtb tb11                                   (AAG to -AG, K503-)
HM776949.1 Mtb tb06                                     (AAG to -AG, K503-)
HM776948.1 Mtb tb05                                     (AAG to -AG, K503-)(ACC
to A-C, T508-)
HM776951.1 Mtb tb10                                (AAG to -AG, K503-)(ACC to A-C,
T508-) (GAC to GTC, D516V)
HM179052.1 Mtb 22BRpoB-TR9
(GAC to GTC, D516V)
HM179051.1 Mtb 21BRpoB-TR9
(GAC to GTC, D516V)
GU904022.1 Mtb Mt647(RIF-R)                                            (CTG
to CCG, L511P)
GU904021.1 Mtb Mt632(RIF-R)
(GAC to GTC, D516V)

FIG. 4H

```
GU904018.1 Mtb Mt466(RIF-R)
(CAA to AAA, Q513K)
GU904016.1 Mtb Mt449(RIF-R)
          (GAC to TAC, D516Y)
AF147033.1 Mtb RJ324(MDR)
(TTC to GTC, F514V)
AF147031.1 Mtb RJ332(MDR)                              (CTG to CCG, L511P; ATG to
ATA, M515I)
AF312235.1 Mtb H180(RIF-R)
(CTG to CTA, L521L)
AF312233.1 Mtb E135(RIF-R)                             (CTG to CCG, L511P; GAC to GGC,
D516G)
AF312232.1 Mtb A9(RIF-R)
(GAC to TTC, D516F)
GU904024.1 Mtb Mt652(RIF-R)                                      (CAA to GAA, Q513E;
GAC to TAC, D516Y)
GU904017.1 Mtb Mt450(RIF-R)
          (GAC to GGC, D516G)
FR828345.1 Mtb MDR-Iran-710 Zabol(RIF-R)       T    C    G C C    A (CGG-TGG,R496W;GTG-GCG,V498A;GCC-GGC,A500G;GCG-CCC,A501P;GAG-AAG,E504K;GGC-
GGT,G507G;ACC-CCC,T508P;AGC-GGC,S512G;ATG-GTG,M515V)
AY587520.1 Mtb(RIF-R)                          C (AAC to CAC, N494H)
(CCAATTCATGG to AG,del between S512&M515)
AF532617.1 Mtb FK119(RIF-R)
(del TTCATG F514&M515)
AB711177.1 Mtb strain MK-11
          (CAA to CAG, Q513Q)
AB711176.1 Mtb strain MK-10                                            (CTG to
TTG, L511L)
AB711172.1 Mtb strain MK-6
(AAC to ATC, N518I)
AB711175.1 Mtb strain MK-9                                    (ATG to ATC,
M515I; GAC to TAC, D516Y)
              L511    Q513    D516
              V  E  A  I  T  P  Q  T  L  I  N  I  R  P  V  V  A  A  I  K  E  F  F
T  S  Q  L  S  Q  F  M  D  Q  N  N  P  L
1206
CGTGAGGCGATCACACCGCAGACGTTGATCAACATCCGGCCGGTGGTCGCCGCGATCAAGGAGTTCTTCGACCAGCAGAGC
TGAGCCAATTCATGGACCAGAACAACCCGCTG SEQ ID NO. 52
AB711174.1 Mtb strain MK-8                                              (AAC to
ATC, N518I; CTG to ATG, L521M)
AB711171.1 Mtb strain MK-5                                              (AAC to
ATC, N518I; CTG to CTC, L521L)
AB711170.1 Mtb strain MK-4                                              (AAC to
ATC, N518I; AAC to GAC, N519D)
AB711169.1 Mtb strain MK-3                                              (GAC to TAC,
D516Y; AAC to ATC, N518I)
AB711167.1 Mtb strain MK-1
(AAC to ATC, N518I)
JN037845.1 Mtb JX084(MDR)
(GAC to TAC, D516Y)
AY308007.1 Mtb 3363P(MDR)
(GAC to GTC, D516V)
          AB711168.1 Mtb strain MK-2
                                                         (AGC to AGA, S509R; AAC to
ATC, N518I)
```

FIG. 4I

```
    S522         H526          S531
     S   G   L   T   H   K   R   R   L   S   A   T   G   P   G   G   L   S   R   E   R   A   G   L   E   V
1321 TCGGGGTTGACCCACAAGCGCCGACTGTCGGCGCTGGGGCCCGGCGGTCTGTCACGTGAGCGTGCCGGGCTGGAGGTC
1398                                                                                SEQ ID NO. 53
JQ414019.1 Mtb SC184(RIF-R)          (TCG to TTG, S531L)
JQ414018.1 Mtb SC65(RIF-R)           (TCG to TTG, S531L)
             (CAC to GAC, H526D)     JQ414017.1 Mtb SC66(RIF-R)
JQ414015.1 Mtb SC120(RIF-R)          (TCG to TTG, S531L)
  (CAC to AAC, H526N)      JQ414012.1 Mtb SC125(RIF-R)
CP003233.1 Mtb RGTB327               (TCG to TTG, S531L)
JN626460.1 Mtb Pk_RIFr4(RIF-R)       (TCG to TTG, S531L)
JN315356.1 Mtb pk_P_3-3(RIF-R)       (TCG to TTG, S531L)
JN315355.1 Mtb pk_P_3-2(RIF-R)       (TCG to TTG, S531L)
JF268611.1 Mtb H37Rv A3              (TCG to TTG, S531L)
JF268610.1 Mtb H37Rv A2              (TCG to TTG, S531L)
JF268608.1 Mtb H37Rv Z               (TCG to TTG, S531L)
JF268607.1 Mtb H37Rv Y               (TCG to TTG, S531L)
JF268600.1 Mtb H37Rv R               (TCG to TGG, S531W)
JF268589.1 Mtb H37Rv G               (TCG to TTG, S531L)
JF268585.1 Mtb H37Rv C               (TCG to TTG, S531L)
CP001642.1 Mtb CCDC5180              (TCG to TTG, S531L)
  (CAC to TAC, H526Y)     HQ377351.1 Mtb CP16
  (CAC to TAC, H526Y)     HQ377345.1 Mtb CJ10
  (CAC to TAC, H526Y)     HQ377344.1 Mtb CI9
  (CAC to TAC, H526Y)     HQ377343.1 Mtb CH8
  (CAC to TAC, H526Y)     HQ377342.1 Mtb CG7
  (CAC to TAC, H526Y)     HQ377341.1 Mtb CF6
  (CAC to TAC, H526Y)     HQ377340.1 Mtb CE5
  (CAC to TAC, H526Y)     HQ377337.1 Mtb CB2
  (CAC to TAC, H526Y)     HQ377336.1 Mtb CA1
  (CAC to GAC, H526D)     HQ286623.1 Mtb MP 39
  (CAC to CTC, H526L)     HQ286622.1 Mtb MP 57
  (CAC to AAC, H526N)     HQ286621.1 Mtb MP 68
HQ286620.1 Mtb MP 38                 (TCG to TGG, S531W)
HQ286619.1 Mtb MP 34                 (TCG to TTG, S531L)
  (CAC to TAC, H526Y)     HM355827.1 Mtb H13407(RIF-R)
  (CAC to TAC, H526Y)     HM355826.1 Mtb H8309(RIF-R)
       (TCG to TTG, S522L)            GQ250580.1 Mtb ZY078(RIF-R)
  (CAC to CGC, H526R)     EF628329.1 Mtb Iran-3062(RIF-R)
EF628318.1 Mtb MDR-Belarus(RIF-R)    (TCG to TTG, S531L)
    (TCG to TTG, S531L) EF628306.1 Mtb MDR-Belarus-388(RIF-R)
            (CAC to CTC, H526L)    EF628304.1 Mtb MDR-Belarus-384(RIF-R)
```

FIG. 4J

```
        S522        H526           S531
     S  G  L  T  H  K  R  R  L  S  A  T  G  P  G  G  L  S  R  E  R  A  G  L  E  V
1321 TCGGGGTTGACCCACAAGCGCCGACTGTCGGCGCTGGGGCCCGGCGGTCTGTCACGTGAGCGTGCCGGGCTGGAGGTC
1398
```

SEQ ID NO. 53

| | |
|---|---|
| CP000717.1 Mtb F11 | (TCG to TTG, S531L) |
| DQ985223.1 Mtb 2937 | (CTG to CCG, L533P) |
| (CAC to TAC, H526Y) | DQ985219.1 Mtb 7 |
| (CAC to TAC, H526Y) | DQ985218.1 Mtb 273 |
| (CAC to TAC, H526Y) | DQ985217.1 Mtb 23 |
| DQ985215.1 Mtb 252 | (TCG to TTG, S531L) |
| (CAC to GAC, H526D) | DQ985214.1 Mtb 15 |
| DQ985213.1 Mtb 1760 | (TCG to TTG, S531L) |
| DQ985212.1 Mtb 1168 | (TCG to TTG, S531L) |
| DQ985211.1 Mtb 646 | (TCG to TTG, S531L) |
| DQ985210.1 Mtb 396 | (TCG to TTG, S531L) |
| DQ985209.1 Mtb 12 | (TCG to TTG, S531L) |
| DQ985208.1 Mtb 1577 | (TCG to TTG, S531L) |
| DQ985207.1 Mtb 574 | (TCG to TTG, S531L) |
| DQ985206.1 Mtb 385 | (TCG to TTG, S531L) |
| DQ985205.1 Mtb 321 | (TCG to TTG, S531L) |
| DQ985204.1 Mtb 282 | (TCG to TTG, S531L) |
| DQ985203.1 Mtb 225 | (TCG to TTG, S531L) |
| DQ985202.1 Mtb 223 | (TCG to TTG, S531L) |
| DQ985201.1 Mtb 216 | (TCG to TTG, S531L) |
| DQ985200.1 Mtb 131 | (TCG to TTG, S531L) |
| DQ985199.1 Mtb 123 | (TCG to TTG, S531L) |
| DQ985198.1 Mtb 24 | (TCG to TTG, S531L) |
| DQ985197.1 Mtb 5 | (TCG to TTG, S531L) |
| AY308015.1 Mtb 4397P(MDR) | (TCG to TGG, S531W) |
| AY308013.1 Mtb 3929P(MDR) | (TCG to TTG, S531L) |
| AY308006.1 Mtb 3052P(MDR) | (TCG to TTG, S531L) |
| (CAC to GAC, H526D) | AY308004.1 Mtb 3005P(MDR) |
| (CAC to CGC, H526R) | AY308001.1 Mtb 2224P(MDR) |
| AY280839.1 Mtb 3041P(MDR) | (TCG to TGG, S531W) |
| AY280836.1 Mtb 3830P(MDR) | (TCG to TTG, S531L) |
| (CAC to GAC, H526D) | AY280835.1 Mtb 3809P(MDR) |
| AY280834.1 Mtb 3796P(MDR) | (TCG to TTG, S531L) |
| AY280833.1 Mtb 3777P(MDR) | (TCG to TTG, S531L) |
| (CAC to CTC, H526L) | AY280829.1 Mtb 3412P(MDR) |
| AY280827.1 Mtb 3228P(MDR) | (TCG to TTG, S531L) |
| AY280826.1 Mtb 3211P(MDR) | (TCG to TTG, S531L) |
| (CAC to TAC, H526Y) | AY280825.1 Mtb 3175P(MDR) |

FIG. 4K

```
              S522        H526           S531
        S   G   L   T     K   R   R   L     A     G  P  G  G  L  S  R  E  R  A  G  L  E  V
   1321 TCGGGGTTGACCCACAAGCGCCGACTGTCGGCGCTGGGGCCCGGCGGTCTGTCACGTGAGCGTGCCGGGCTGGAGGTC
   1398                                                                  SEQ ID NO. 53
   AY280824.1 Mtb 3159P(MDR)         (TCG to TGG, S531W)
   AY280823.1 Mtb 3002P(MDR)         (TCG to TTG, S531L)
   AY280820.1 Mtb 2795P(MDR)         (TCG to TTG, S531L)
   AY280818.1 Mtb 2503P(MDR)         (TCG to TGG, S531W)
   AY280817.1 Mtb 2485P(MDR)         (TCG to TTG, S531L)
   AY280814.1 Mtb 2023P(MDR)         (TCG to TTG, S531L)
   AY280813.1 Mtb 1928P(MDR)         (TCG to TTG, S531L)
   AY280811.1 Mtb  164P(MDR)         (TCG to TTG, S531L)
      (CAC to GAC, H526D)       AY280810.1 Mtb 1237P(MDR)
   AY280807.1 Mtb  106P(MDR)         (TCG to TTG, S531L)
   AY271377.1 Mtb   61P(MDR)         (TCG to TTG, S531L)
      (CAC to TAC, H526Y)       AY271376.1 Mtb 2868P(MDR)
   AY271373.1 Mtb 2472P(MDR)         (TCG to TTG, S531L)
   AY271371.1 Mtb 2455P(MDR)         (TCG to TTG, S531L)
   AY271370.1 Mtb 1902P(MDR)         (TCG to TTG, S531L)
      (CAC to CAA, H526Q)       AY280846.1 Mtb LUK/PCM/100(RIF-R)
   AY280845.1 Mtb LUK/HOS/66(RIF-R)  (TCG to TTG, S531L)
   AY280844.1 Mtb LUK/HOS/48(RIF-R)  (TCG to TTG, S531L)
   AY280842.1 Mtb LUK/HOS/92(RIF-R)  (TCG to TTG, S531L)
      (CAC to GAC, H526D)       AY280841.1 Mtb LUK/DTC/91(RIF-R)
   AY147218.1 Mtb 368(MDR)           (CTG to CCG, L533P)
      (TCG to CCG, S522P)         AY147215.1 Mtb 60b(MDR)
   AY147212.1 Mtb 265                           (CTG to CCG, L538P)
   AY155360.1 Mtb C29(MDR)           (CTG to CCG, L533P)
   AY155359.1 Mtb C28(MDR)           (TCG to TGG, S531W)
   AY155356.1 Mtb TCVGH22(MDR)       (TCG to TTG, S531L)
      (CAC to TAC, H526Y)       AJ318814.1 Mtb 1058-97(RIF-R)
   AY898740.1 Mtb 490-0(DR)          (TCG to TTG, S531L)
   AY544973.1 Mtb CIP 105795         (TCG to TTG, S531L)
   HQ286618.1 Mtb MP11(RIF-R)        (CTG to CCG, L533P)
      (CAC to CGC, H526R)       HQ286616.1 Mtb MP08(RIF-R)
      (CAC to CTC, H526L)       HQ286615.1 Mtb MP02(RIF-R)
   HQ286614.1 Mtb MP06(RIF-R)        (TCG to TGG, S531W)
   HQ286613.1 Mtb MP10(RIF-R)        (TCG to TTG, S531L)
      (CAC to GAC, H526D)       AY280828.1 Mtb 3348P(MDR)
   CP001976.1 Mtb KZN 605             (CTG to CCG, L533P)
         (TCG to GTG, S522V)            HQ286628.1 Mtb MP 76(MDR)
```

FIG. 4L

```
       S522         H526         S531
     S  G  L  T  H  K  R  R  L  S  A  G  P  G  G  L  S  R  E  R  A  G  L  E  V
1321 TCGGGGTTGACCCACAAGCGCCGACTGTCGGCGCTGGGGCCCGGCGGTCTGTCACGTGAGCGTGCCGGGCTGGAGGTC
1398                                                                SEQ ID NO. 53
```

(CAC to GGC, H526G)    HM345980.1 Mtb PSGMYBL 01(RIF-R)
HM239777.1 Mtb         (TCG to TTG, S531L)
GQ293224.1 Mtb(DR)     (TCG to CAG, S531Q)
                       (TCG to TTG, S531L)    EF661863.1 Mtb H37Rv from Iran(DR)
       (GCG to TGG, A532W)    EF628348.1 Mtb MDR-Iran-23 Zabol(RIF-R)
(CAC to GAC, H526D)    EF628328.1 Mtb MDR-Belarus-489 vitebsk(RIF-R)
(CAC to CTC, H526L)    EF628323.1 Mtb Belarus-414 Minsk(RIF-R)
       (GGG to GCG, G523A)    EF628316.1 Mtb Belarus-139(RIF-R)
       (GGG to GCG, G523A; CAC to GAC, H526D) EF628315.1 Mtb Belarus-7285(RIF-R)
(CAC to CTC, H526L)    EF628310.1 Mtb Belarus-414(RIF-R)
AY280831.1 Mtb 3599P(MDR)    (TCG to TTG, S531L)
AY271369.1 Mtb 1760P(MDR)    (TCG to TTG, S531L)
AY147217.1 Mtb 724(MDR)      (TCG to TAC, S531Y)
(CAC to GCC, H526A)    AY147216.1 Mtb 333(MDR)
(CAC to TGC, H526C)    AY155357.1 Mtb TCVGH26(MDR)
AY188815.1 Mtb 2540-97(RIF-R)    (TCG to TTG, S531L)
AY823317.1 Mtb MDR25(MDR)    (TCG to TTC, S531F)
AY823310.1 Mtb MDW108(MDR)   (TCG to GTG, S531V)
       (TCG to TTG, S531L)    EF628294.1 Mtb MDR-Belarus-367-Minsk(RIF-R)
(CAC to TAC, H526Y)    AY819714.1 Mtb 333-3(DR)
       (GCGCT to CGCTT between A532 and L533)    EF628336.1 Mtb Belarus-23623 Brest(RIF-R)
       (CGGCGCT to GCCGCTT between S531 and L533)    EF628335.1 Mtb MDR-Belarus-n1217 Brest(RIF-R)
(GGG to GGC, G523G)    EF628317.1 Mtb MDR-Belarus-94(RIF-R)
       (TCG to TTG, S531L; CTG to -TG, L533)
EF628295.1 Mtb MDR-Belarus-447-Minsk(RIF-R)
AY823315.1 Mtb 3MDRW41(MDR)    (TCG to GGG, S531G)
(CAC to CGA, H526R)    AY823314.1 Mtb MDR24(MDR)
       (CAC to GGC, H526G)    AY823312.1 Mtb MDR137(MDR)
       (GCG to TGG, A532W)    EF628344.1 Mtb Iran-90 Tehran(RIF-R)
(CAC to TGC, H526C)    AY823316.1 Mtb MDR97(MDR)
       (GCGCT to TGGGC between A532 and L533)    EF628359.1 Mtb Iran-103 Zabol(RIF-R)
       (GGG to GGC, G523G)    (TCG to TTG, S531L; GCGCT to CGCTT between A532 and L533) EF628338.1 Mtb Belarus-24275(RIF-R)
       (GGG to GCG, G523A)    (GCG to TGG, A532W; CTG to GTG, L533V)
EF628332.1 Mtb Belarus-1416 Brest(RIF-R)
(GGG to GGA, G523G)    EF628309.1 Mtb MDR-Belarus-468(RIF-R)
AY271372.1 Mtb 2459P(MDR)    (TCG to TTG, S531L)
AY188816.1 Mtb 1255-98(RIF-R)    (CTG to ATG, L530M; TCG to TTC, S531F)
       (GGG to GCG, G523A; TCG to TTG, S531L) EF628342.1 Mtb Iran-3708(RIF-R)
       (GGG to GCG, G523A; TCG to TTG, S531L) EF628340.1 Mtb MDR-Iran-163(RIF-R)

```
       S522         H526         S531
     S  G  L  T  H  K  R  R  L  S  A  G  P  G  G  L  S  R  E  R  A  G  L  E  V
1321 TCGGGGTTGACCCACAAGCGCCGACTGTCGGCGCTGGGGCCCGGCGGTCTGTCACGTGAGCGTGCCGGGCTGGAGGTC
1398                                                                SEQ ID NO. 53
```

(GGG to GCG, G523A; TCG to TTG, S531L) EF628339.1 Mtb Iran-441(RIF-R)
(CAC to TAC, H526Y)    AY271365.1 Mtb 1230P(MDR)
(CAC to CGC, H526R)    (GCG to TGG, A532W; CTG to GGG, L533G)
       EF628360.1 Mtb MDR-Iran-36-Teh(RIF-R)
       (GGG to GCG, G523A)         C    (GCG to TGG, A532W; GGG to GGC, G534G) EF628347.1 Mtb Iran-290(RIF-R)
       (GGG to GCG, G523A)    (TCG to TTG, S531L; CTG to TGG, L533W)
EF628338.1 Mtb Belarus-469 Magilev(RIF-R)
       (GCGCT to CGCTT between A532 and L533)    EF628337.1 Mtb MDR-Belarus-3255 Brest(RIF-R)
(CAC to GAC,H526D)    (GCG to TGG, A532W; CTG to GTG, L533V)    EF628333.1 Mtb MDR-Belarus-2262 Brest(RIF-R)

FIG. 4M

▓ ▓ (GCG to TGG, A532W; CTG to GTG, L533V)   ▓▓628330.1 Mtb MDR-Belarus-2715 Brest(RIF-R)
        (GCG to GTG, A532V) ▓ ▓▓  C (CTG to GGG, L533G; GGG to GGC, G534G)
▓▓628311.1 Mtb MDR-Belarus-407(RIF-R)
▓ (GGG-GCG,G523A) ▓  ▓ (CGA to CCA, R529P; TCG to TTG, S531L)   ▓▓628308.1 Mtb MDR-Belarus-402(RIF-R)
             ▓ (GGG to GCC, G523A; CGA to CCA, R529P) ▓▓628307.1 Mtb MDR-Belarus-412(RIF-R)
(CAC to CTC,H526L) ▓       ▓▓ ▓▓ (GCG to TGG, A532W; CTG to GGG, L533G)
       ▓▓628306.1 Mtb MDR-Belarus-1414(RIF-R)
 (CAC to GAC, H526D)▓     ▓▓ ▓▓ (GCG to TGG, A532W; CTG to GGG, L533G)
       ▓▓628283.1 Mtb MDR(RIF-R)
AY280843.1 Mtb LUK/ROS/134(RIF-R) ▓ (TCG to TTG, S531L)
        ▓▓ ▓▓ (GCG to TGG, A532W; CTG to GGG, L533G)   ▓▓628332.1 Mtb 633 Tehran(RIF-R)
AY319713.1 Mtb 147-3(DR)        ▓ (CTG to CCG, L533P)
   (ACCCAC to AC▓CCAC between T525 and H526) EU325648.1 Mtb(RIF-R)
      ▓ (CGA to CTA, R529L) JN819067.1 Mtb 2001-1669 mutant2
   ▓ (CAC to CGC, H526R)  HQ844253.1 Mtb DR-TB1(DR)
HQ844252.1 Mtb DR-TB2(DR)  ▓ (TCG to TTG, S531L)
▓  (CAC to GAC, H526D)  HQ844251.1 Mtb MDR-TB2(MDR)
▓  (CAC to TAC, H526Y)  HQ844249.1 Mtb MDR-TB4(MDR)
HQ844244.1 Mtb MDR-TB3(MDR)       ▓ (TCG to TTG, S531L)
  ▓ (CAC to CGC, H526R)  HQ844243.1 Mtb MDR-TB1(MDR)
▓    ▓(GGG to GCG,G523A;CAC to TAC,H526Y;GCGCT to TGGGC between A532 and L533)
▓▓628357.1 Mtb Iran-167 Tehran(RIF-R)
(CAC to CGC,H526R) ▓        ▓▓ ▓▓  A (GCG to TGG,A532W;CTG to GGG,L533G;GGG-GGA,G534G) ▓▓628356.1 Mtb 108 Tehran(RIF-R)
    (GCGCT to TGGGC between A532 and L533) A (GGG-GGA,G534G) ▓▓628354.1 Mtb 19 Kerman(RIF-R)
                 ▓▓ ▓▓  C (GCG-TGG,A532W;CTG to GGG,L533G;GGG-GGC,G534G)▓▓628346.1 Mtb Iran-29 Tehran(RIF-R)
        ▓                ▓▓ ▓(ACC-AAC,T525N;GCG-TGG,A532W;CTG-GTG,L533V) ▓▓628331.1 Mtb MDR-Belarus-85 vitebsk(RIF-R)
        ▓(CAC to GAC,H526D) ▓ ▓▓ (GCG to GGG, A532G; CTG to GGG, L533G)
▓▓628336.1 Mtb MDR-Belarus-894 vitebsk(RIF-R)
   ▓(CAC to GAC,H526D) ▓ ▓▓ (GCG to GTG, A532V; CTG to GGG, L533G)
▓▓628325.1 Mtb MDR-Belarus-507 Magilev(RIF-R)
    ▓(GGG to GGC, G523G)   ▓  ▓▓ (TCG-TTG,S531L;GCG-GTG,A532V;CTG-GGG,L533G)▓▓628324.1 MtbMDR-Belarus-442Magilev(RIF-R)
        ▓(CAC to GAC,H526D)▓▓ ▓▓ (GCG to TGG, A532W; CTG to GGG, L533G)
    ▓▓628322.1 Mtb MDR-Belarus-443 Minsk(RIF-R)
        ▓(CAC to GAC,H526D)▓▓ ▓▓ (GCG to TGG, A532W; CTG to GGG, L533G)
    ▓▓628321.1 Mtb MDR-443-Minsk(RIF-R)
        ▓(CAC to CTC,H526L)▓ ▓▓   C (GCG-GGG,A532G;CTG-GGG,L533G;GGG-GGC,G534G) ▓▓628319.1 Mtb MDR-85-vitebsk(RIF-R)
(GGG-GCG,G523A)▓    ▓(CAC to GAC,H526D) ▓ ▓▓   C (GCG-GTG,A532V;CTG-GGG,L533G;GGG-GGC,G534G) ▓▓628313.1 Mtb MDR-Belarus (RIF-R)
        ▓(CAC to GAC,H526D)▓▓ ▓▓ (GCG to TGG, A532W;CTG to GGG, L533G) ▓▓628301.1 Mtb MDR-Belarus-443 (RIF-R)
     ▓ (GGG to GCG, G523A)      ▓  ▓▓ (TCG to TTG, S531L; CTG to TGG, L533W)▓▓628358.1 Mtb MDR-Iran-93/1384(RIF-R)
          (CAAGCGCC-ACAACC in H526-R529) G(CCC to CCG, P535P)
▓▓628350.1 Mtb Iran-1757 PII(RIF-R)

S522       H526         S531   ▓▓
  S  G  L  T  ▓  K  R  R  L  ▓  A  ▓  G  P  G  G  L  S  R  E  R  A  G  L  E  V
1321 TCGGGGTTGACCCACAAGCGCCGACTGTCGGCGCTGGGGCCCGGCGGTCTGTCACGTGAGCGTGCCGGGCTGGAGGTC
1398                                                       SEQ ID NO. 53
         ▓          ▓            ▓▓ ▓▓(GGG-GCG,G523A;CAC-GAC,H526D;GCG-TBG,A532-;CTG-GKG,L533-;GGG-GG-,G534-)▓▓628298.1 Mtb

MDR-Belarus-411(RIF-R)
      (GCGCT to TGGGC between A532 and L533) A(GGG to GGA, G534G) ▓▓628368.1 Mtb MDR-Iran-33 PII(RIF-R)
        ▓                          A((GCGCT-TGGGC in A532&L533; GGG-GGA,G534G) ▓▓628366.1 Mtb MDR-Iran-165 Zabol(RIF-R)
       (GGG-GCG,G523A;CAC-TAC,H526Y)

FIG. 4N

A(GCG-TGG,A532W;CTG-GGG,L533G;GGG-GGA,G534G) EF628351.1 Mtb MDR-Iran-161 Zabol(RIF-R)
(GGG-GCG,G523A;CAC-TAC,H526Y)
(GGG-GCG,G523A)         C(GCGCT-TGGGC in A532&L533; GGG to GGC, G534G) EF628343.1 Mtb Iran-3458(RIF-R)
(CAC-GAC,H526D)    (GCG-TGG,A532W; CTGGGGCCC to GGGCGCCCC in L533&P535) EF628327.1 Mtb MDR-932(RIF-R)
(CAC-GAC,H526D)    (GCG to TGG, A532W; CTG to GGG, L533G) EF628320.1 Mtb Belarus-455 Minsk(RIF-R)
(CTGGGGCCC to GGTGGCCCC in L533&P535) EF628331.1 Mtb MDR-Belarus-2548 M(RIF-R)
(GGG-GCG,G523A;CAC-GAC,H526D) (GCG-GTG,A532V)
(GGG to GCG, G523A)    A(GCGCT-TGGGC in A532&L533;GGG-GGA,G534G) EF628367.1 Mtb MDR-Iran-303-281Mashad(RIF-R)
(AAGCGC to AA-C-C in K527-R528)    G (TCG to TTC, S531F; CCC to CCG,P535P) EF628348.1 Mtb MDR-Iran-36 asli Iran(RIF-R)
A(GCGCT-TGGGC in A532&L533;GGG-GGC,G534G) EF628364.1 Mtb Iran-3542(RIF-R)
(GCG-TGG,A532W;CTG-GGG,L533G) EF628303.1 Mtb MDR-Belarus-571(RIF-R)
(GGG-GCG,G523A;CAC-GAC,H526D)
(TCG to TTG, S531L; GCG-TGG,A532W;CTG-GGG,L533G) EF628302.1 Mtb MDR-Belarus-453(RIF-R)
(GGG-GCG,G523A;CAC-GAC,H526D)
(TCG to TTT, S531F)    HM048903.1 Mtb MDR CaseYA66
(GGG-GCG,G523A;CAC-GAC,H526D;CGCTGG to -G-GGR between A532 and G534)    EF628336.1 Mtb MDR-Belarus-4(RIF-R)
(CAC to AGC, H526S)    DQ205441.1 Mtb TBM621(RIF-R)
DQ205440.1 Mtb TBM554(RIF-R)    (CTG to CCG, L533P)
AY308008.1 Mtb 3444P(MDR)    (TCG to TTG, S531L)
AY271368.1 Mtb 168P(MDR)    (TCG to TTG, S531L)
AF392115.1 Mtb(RIF-R)    (CTG to CCG, L533P)
(GGG to GCG,G523A;GCGCTGGGG to TGGCGC-GGT- between A532 and G534) EF628363.1 Mtb Iran-173 Zabol(RIF-R)
AJ318815.1 Mtb 2540-97(RIF-R)    (TCG to TTG, S531L)
DQ205438.1 Mtb TBM301(RIF-R)    (CTG to ATG, L530M; TCG to TTC, S531F)
AY308003.1 Mtb 2796P(MDR)    (TCG to TTG, S531L)
AY280819.1 Mtb 2633P(MDR)    (TCG to TGG, S531W)
(CCACA to GTCCC between T525 and K527) HQ997367.1 Mtb Seq194767
(CAC to G-C at H526; CGGCGCT to TCTGGGC between S531 and L533) EF628365.1 Mtb MDR-Iran-159(RIF-R)
DQ205439.1 Mtb TBM552(RIF-R)    (TCG to GGG, S531G)    G (GAG to GGG, E541G)
(CAC to GAC, H526D)    AY280838.1 Mtb 6009P(MDR)
AF360401.1 Mtb Rm33(RIF-R)    (CTG to CCG, L533P)
(CAC to CAA, H526Q)    AF360400.1 Mtb Rm09(RIF-R)
(CAC to GAC, H526D)    AF055892.1 Mtb Rm16(MDR)

S522        H526        S531
  S  G  L  T     K  R  R  L     A     G  P  G  G  L  S  R  E  R  A  G  L  E  V
1321 TCGGGGTTGACCCACAAGCGCCGACTGTCGGCGCTGGGGCCCGGCGGTCTGTCACGTGAGCGTGCCGGGCTGGAGGTC 1398

SEQ ID NO. 53

(GGG to GCG,G523A)    A (GCGCT to TGGGC in A532 & L533;GGG to GGA,G534G) EF628355.1 Mtb 10-2 Tehran(RIF-R)
(CAC to TAC, H526Y; TCG to TTG, S531L) EF628341.1 Mtb Iran-163 Tehran(RIF-R)
(CGA to CCA, R529P; CTG to TGG, L533W) EF628314.1 Mtb MDR-Belarus-408(RIF-R)
(TCG to TTG, S531L) FJ915185.1 Mtb 331102070029
(CAC to TAC, H526Y)    AY325127.1 Mtb 4540EHS
(TCG to TTG, S531L) AY325125.1 Mtb 270EHS
(GGG to TGG, G523W; ACC to ATC, T525I) AF055801.1 Mtb Rm19(MDR)
(CAC to CGC, H526R)    U70422.1 Mtb(DR)
T    G EF628362.1 Mtb MDR-Iran-600 Tehran(RIF-R)
(ACC-ACG,T525T;CAC-TTC,H526F;GCG-TGG,A532W;CTG-CGG,L533R;GGG-GGT,G534G;TCA-TGA,S539end)

FIG. 40

```
                                    C              G              Mtb MDR-
Iran-663 kerman(RIF-R))
         (ACC-ACG,T525T;CAC-TTC,H526F;GCG-TGG,A532W;CTG-CGG,L533R;GGG-
GGC,G534G;TCA-TGA,S539end)
                     (CAC to CGC, H526R)    FJ915188.1 Mtb 331122070013
                     (CAC to CAA, H526Q)             Mtb 331102070021
                            (TCG to TTG, S531L) AY325126.1 Mtb 507EHS
                            (TCG to TTG, S531L) AY308014.1 Mtb 3993P(MDR)
                     (CAC to TAC, H526Y)   HM776955.1 Mtb tb14
                     (CAC to CGC, H526R)   HM776954.1 Mtb tb13
                            (TCG to TTG, S531L) HM776953.1 Mtb tb12
                            (TCG to TTG, S531L) HM776950.1 Mtb tb08
                            (TCG to TTG, S531L) AY308011.1 Mtb
3538P(MDR)
                            (TCG to TTG, S531L; CTG to -TG, L533-)
EF628297.1 Mtb MDR-Belarus-2331(RIF-R)
                     (CAC to TAC, H526Y)   FJ915167.1 Mtb L17
                     (CAC to CTC, H526L)   FJ915186.1 Mtb 331102070019
                     (CAC to TAC, H526Y)             Mtb tb11
                            (TCG to TTG, S531L)             Mtb tb06
                            (TCG to TTG, S531L) AY325128.1 Mtb 6852EHS
                            (TCG to TTG, S531L) HM179058.1 Mtb 30BRpoB-TR9
                     (CAC to TAC, H526Y)   HM179055.1 Mtb 26BRpoB-TR9
                            (TCG to TGG, S531W) HM179047.1 Mtb 14BRpoB-TR9
                            (TCG to TTG, S531L) HM179046.1 Mtb 13BRpoB-
TR9
                            (TCG to TTG, S531L) HM179045.1 Mtb 12BRpoB-
TR9
                            (TCG to TTG, S531L) HM179043.1 Mtb 8BRpoB-
TR9
                            (TCG to TTG, S531L) HM179043.1 Mtb 8BRpoB-
TR9
                            (TCG to TTG, S531L) HM179042.1 Mtb 7BRpoB-
TR9
                            (TCG to TTG, S531L) HM179041.1 Mtb 6BRpoB-
TR9
                            (TCG to TTG, S531L) HM179038.1 Mtb
RpoB3135-TR9
  (CAC to GAC, H526D)       HM179037.1 Mtb RpoB3123-TR9
                            (TCG to TTG, S531L) HM179035.1 Mtb
RpoB3099-TR9
   S522         H526       S531
    S  G  L  T  H  K  R  R  L  S  A  T  G  P  G  G  L  S  R  E  R  A  G  L  E  V
1321 TCGGGGTTGACCCACAAGCGCCGACTGTCGGCGCTGGGGCCCGGCGGTCTGTCACGTGAGCGTGCCGGGCTGGAGGTC
1398                                                                  SEQ ID NO. 53
                     (CAC to CGC, H526R)   HM179032.1 Mtb RpoB3023-TR9
                            (TCG to TTG, S531L) HM179030.1 Mtb
RpoB2984-TR9
                            (TCG to TTG, S531L) HM179029.1 Mtb
RpoB2903-TR9
                     (CAC to CTC, H526L)   GU904020.1 Mtb Mt582(RIF-R)
                            (TCG to TGG, S531W) GU904014.1 Mtb Mt340(RIF-R)
                            (CTG to CCG, L533P) GU904013.1 Mtb
Mt306(RIF-R)
                     (CAC to TAC, H526Y)   GU904012.1 Mtb Mt254(RIF-R)
   (CAC to GAC, H526D)    GU904011.1 Mtb Mt220(RIF-R)
                            (TCG to TTG, S531L) GU904010.1 Mtb Mt213(RIF-R)
       (CAC to GGC, H526G)       C (GGC to CGC, G536R) FJ915183.1 Mtb strain
331121080004 mutant(RIF-R)
                            (TCG to TTG, S531L)             Mtb
RJ324(MDR)
                            (CTG to CCT, L533P) AF143771.1 Mtb(MDR)
                     (CAC to CGC, H526R; CGA to CAA, R529Q)              
Mtb G70(RIF-R)
                     (CAC to TAC, H526Y)             Mtb H180(RIF-R)
                            (CTG to CCG, L533P) AF312234.1 Mtb
F519(RIF-R)
                     (CAC to TGC, H526C)   GU904023.1 Mtb Mt651(RIF-R)
                    FIG. 4P
```

[GU904019.1] Mtb Mt510(RIF-R) (CAC to TAC, H526Y; TCG to TTG, S531L)
(CGA to CAA, R529Q) [GU904017.1] Mtb Mt450(RIF-R)
(CAC to CGC, H526R; CGA to CAA, R529Q)
[GU904015.1] Mtb Mt437(RIF-R)

C [EF628346] Mtb MDR-Iran-710 Zabol(RIF-R)      C      A      A
(GGG-GCG,G523A;CAC-CAA,H526Q) (GCGCT to TGGGC in A532&L533;GGG-GGC,G534G;GAG-GAA,E541E;GCC-GAC,A543D;CTG-CTC,L545L)
(TGACCCACA to GGCCCC in L524 & K527) AF147034 Mtb RJ371(MDR)
(CTG to CCG, L533P) AY308012.1 Mtb 3614P(MDR)
(CAC to CGC, H526R) AB711178.1 Mtb strain MK-12
(CAC to CTC, H526L) AB711173.1 Mtb strain MK-7
(TCG to TTG, S531L) JN210555.1 Mtb JX099(MDR)
(TCG to TTG, S531L) JN210554.1 Mtb JX101(MDR)
(TCG to TTG, S531L) JN037846.1 Mtb JX089(MDR)
(TCG to TTG, S531L) AY308009.1 Mtb 3477P(MDR)
(CAC to CGC, H526R) [AB711167.1] Mtb strain MK-1
(CAC to TAC, H526Y) [AB711168.1] Mtb strain MK-2

FIG. 4Q

COMPOSITIONS AND METHODS FOR IDENTIFYING DRUG RESISTANT TUBERCULOSIS

CROSS-REFERENCE TO RELATED APPLICATIONS

This application is a divisional of U.S. patent application Ser. No. 15/209,453, filed Jul. 13, 2016, which claims priority to U.S. provisional patent application Ser. No. 62/192,446, filed Jul. 14, 2015, which is incorporated herein by reference in its entirety.

TECHNICAL FIELD

Provided herein are compositions and methods for diagnosing and characterizing tuberculosis infection. In particular, provided herein are compositions and methods for identifying drug resistant tuberculosis.

BACKGROUND

Tuberculosis (TB) is an infectious disease that affects mainly the lungs (pulmonary TB), A person with pulmonary TB is infectious to others, without treatment this person may infect 10-15 persons/year.

TB is closely connected with HIV, People living with HIV are about 37 times more likely to develop TB than HIV negative people. In 2009, TB accounted for 25% of deaths among HIV-positive people. Developing countries especially with high HIV prevalence are the high burden TB areas.

More than 90% of people with drug-susceptible TB can be cured in six months using combinations of first-line drugs such as Rifampicin and isoniazid. Inadequate treatment, low compliance or intermittent therapy may lead to development of resistance against the first line drugs. Sometimes even the primary infection occurs with resistant MTB bacteria.

The recommended treatment of new-onset pulmonary tuberculosis, as of 2010, is six months of a combination of antibiotics containing rifampicin, isoniazid, pyrazinamide, and ethambutol for the first two months, and only rifampicin and isoniazid for the last four months. Where resistance to isoniazid is high, ethambutol may be added for the last four months as an alternative. If multiple drug-resistant TB is detected, treatment with at least four effective antibiotics for 18 to 24 months is recommended.

Primary resistance occurs when a person becomes infected with a resistant strain of TB. A person with fully susceptible TB may develop secondary (acquired) resistance during therapy because of inadequate treatment, not taking the prescribed regimen appropriately (lack of compliance), or using low-quality medication. Drug-resistant TB is a serious public health issue in many developing countries, as its treatment is longer and requires more expensive drugs. MDR-TB is defined as resistance to the two most effective first-line TB drugs: rifampicin and isoniazid. Extensively drug-resistant TB is also resistant to three or more of the six classes of second-line drugs. Totally drug-resistant TB is resistant to all currently used drugs. It was first observed in 2003 in Italy, but not widely reported until 2012 and has also been found in Iran and India.

Treatment of MDR-TB with second line drugs is more challenging, more costly, causes more severe side effects, and must be taken for up to two years. Cure rates for MDR-TB are lower, typically ranging from around 50% to 70%.

It is important to identify patients with TB resistant bacteria to start immediate treatment and reduce the spread of the resistant MTB.

SUMMARY

Provided herein are compositions and methods for diagnosing and characterizing tuberculosis infection. In particular, provided herein are compositions and methods for identifying drug resistant tuberculosis.

For examples, in some embodiments, the present disclosure provides a method of detecting the antibiotic resistance of Mycobacterium complex (MTB) in a subject, comprising at least one of: contacting the sample with one or more reagents for detection of the presence of rifampicin and isoniazid resistance genes; and performing a rifampicin and isoniazid resistance detection assay with the reagents. In some embodiments, the reagents are, for example, one or more nucleic acid primers and one or more nucleic acid probes. In some embodiments, the assay further comprises the steps of contacting a sample from a subject with one or more reagents for detecting the presence of MTB; and performing an MTB detection assay with the reagents. In some embodiments, the MTB detection assay is performed prior to the rifampicin and isoniazid resistance detection assay. In some embodiments, the MTB detection assay and the rifampicin and isoniazid resistance detection assay are nucleic acid amplification assays (e.g., real time PCR). In some embodiments, the rifampicin and isoniazid resistance detection assay detects mutations in one or more target regions selected from, for example, rpoB RRDR, katG or inhA upper stream promoter. In some embodiments, the mutations in rpoB are mutations at one or more amino acids selected from, for example, D516V, H526Y, H526D, or S531L. In some embodiments, the katG mutation is amino acid change S315T1 and the inhA upper stream promoter mutation is the nucleic acid mutation C-15T, In some embodiments, the MTB detection assay detects one or more target regions selected from IS6110 or PAB. In some embodiments, the first and second reagents are one or more of SEQ ID NOs: 1-21. In some embodiments, the sample is, for example, sputum, bronchoalveolar lavage (BAL), or N-acetyl-L-cystine (NALC) sediment. In some embodiments, the MTB is one or more species of Mycobacterium selected from, for example, Mycobacterium tuberculosis, Mycobacterium africanum, Mycobacterium bovis, Mycobacterium bovis BCG, Mycobacterium canettii, Mycobacterium microti, Mycobacterium caprae, or Mycobacterium pinipedii. In some embodiments, the method further comprises the step of diagnosing infection by MTB in the subject based on the results of the MTB detection assay. In some embodiments, the method further comprises the step of identifying the MTB as resistant to rifampicin and/or isoniazid based on the rifampicin and isoniazid resistance detection assay. In some embodiments, the MTB detection assay is performed prior to the rifampicin and isoniazid detection assay. In some embodiments, the method further comprises the step of determining a treatment course of action based on the results of the MTB detection assay and the rifampicin and isoniazid detection assay. In some embodiments, the method further comprises the step of administering the treatment. In some embodiments, the treatment comprises a combination of antibiotics administered for 6 months (e.g., antibiotics that the subject is not resistant to). In some embodiments, the method further comprises the step of repeating the detections steps one or more times during or following the treatment.

Further embodiments provide a method of detecting the presence and antibiotic resistance of *Mycobacterium* complex (MTB) in a subject, comprising: a) contacting a sample from a subject with one or more first reagents for detecting the presence of MTB; h) performing an MTB detection assay with said first regents; c) contacting said sample with one or more second reagents for detection of the presence of rifampicin and isoniazid resistance genes; d) performing a rifampicin and isoniazid resistance detection assay with said second reagents; and e) determining a treatment course of action based on the results of said MTB detection assay and said rifampicin and isoniazid detection assay.

Yet other embodiments provide a kit, comprising: one or more reagents for detection of the presence of rifampicin and isoniazid resistance genes and optionally one or more reagents for detecting the presence of MTB. In some embodiments, the kit further comprises one or more additional components selected, for example, control nucleic acids, buffers, nucleic acid polymerases, or instructions.

Additional embodiments are described herein.

DESCRIPTION OF THE FIGURES

FIGS. 3A through 3AF show results of rifampicin and isoniazid detection for drug sensitive and drug resistant bacteria.

DETAILED DESCRIPTION

Figure 1:
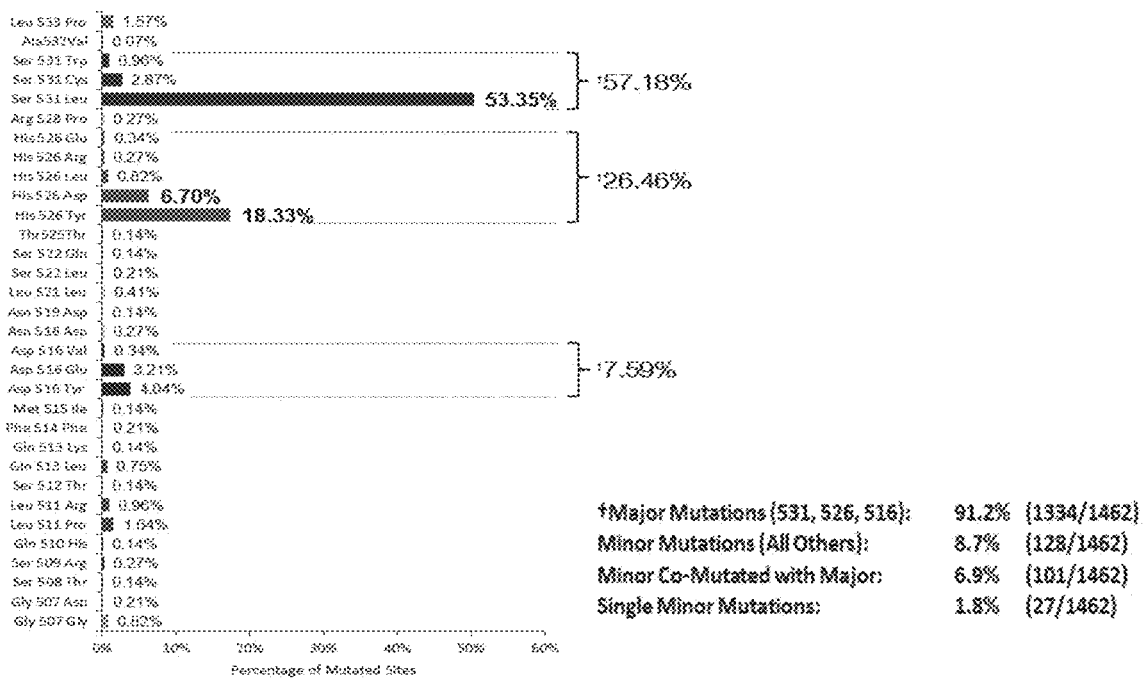
FIG. 1 shows determination of relevant rpoB mutations.

Provided herein are compositions and methods for diagnosing and characterizing tuberculosis infection. In particular, provided herein are compositions and methods for identifying drug resistant tuberculosis.

Definitions

As used herein, "a" or "an" or "the" can mean one or more than one. For example, "a" widget can mean one widget or a plurality of widgets.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl¬methyl) uracil, 5-fluorouracil, 5 bromouracil, 5-carboxymethylaminomethyl 2 thiouracil, 5 carboxymethyl¬aminomethyluracil, dihydrouracil, inosine, N6 isopentenyladenine, 1 methyladenine, 1-meshylpseudo¬uracil, 1 methylguanine, 1 methylinosine, 2,2-dimethyl¬guanine, 2 methyladenine, 2 methylguanine, 3-methyl¬cytosine, 5 methylcytosine, N6 methyladenine, 7 methyluianine, 5 methylaminomethyluracil, 5-methoxy¬amino¬methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxy acetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "amplicon" refers to a nucleic acid generated via amplification reaction. The amplicon is typically double stranded DNA; however, it may be RNA and/or DNA:RNA. The amplicon comprises DNA complementary to a sample nucleic acid. In some embodiments, primer pairs are configured to generate amplicons from a sample nucleic acid. As such, the sequence of any given amplicon may include the primer pair, the complement of the primer pair, and the region of a sample nucleic acid that was amplified to generate the amplicon. One skilled in the art understands that the incorporation of the designed primer pair sequences into an amplicon may replace the native sequences at the primer binding site, and complement thereof. In certain embodiments, after amplification of the target region using the primers the resultant amplicons having the primer sequences are used for subsequent analysis. In some embodiments, the amplicon further comprises a length that is compatible with subsequent analysis.

The term "amplifying" or "amplification" in the context of nucleic acids refers to the production of multiple copies of a polynucleotide, or a portion of the polynucleotide, typically starting from a small amount of the polynucleotide (e.g., as few as a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "solid support" refers to a substrate or other solid material that does not dissolve in aqueous solutions utilized in nucleic acid purification or isolation. For example, in some embodiments, solid supports are substrates utilized in nucleic acid purification and isolation. Examples include, but are not limited to, beads, particles, resins, chromatography columns, and the like. In some embodiments, solid supports are coated or functionalized with material that enhances nucleic acid binding.

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids (e.g., sputum), solids, tissues, and gases. Biological samples include blood products, such as plasma, serum, and the like. In some embodiments, samples comprise cells (e.g., bacterial cells) tissues, or nucleic acids (e.g., DNA or RNA) isolated from such cells or tissues. Environmental samples include environmental material such as surface matter, soil, mud, sludge, biofilms, water, and industrial samples. Such examples are not however to be construed as limiting the sample types applicable to the present disclosure.

Embodiments of the Technology

Although the disclosure herein refers to certain illustrated embodiments, it is to be understood that these embodiments are presented by way of example and not by way of limitation.

I. Detection Assays

Embodiments of the present disclosure provide a multi-part assay for detection of the presence of antibiotic resistant MTB and optionally MTB. In some embodiments, the assay first detects the presence or absence of an MTB complex bacterium (e.g., including but not limited to, one or more of *M. tuberculosis, M. africanum, M. bovis, M. bovis BCG, M. canettii, M. microti, M. caprae,* and *M. pinnipedii*). The present disclosure is not limited to particular MTB targets. Examples include, but are not limited to, IS6110 or PAB. The Genhank accession number for IS6110 is X17348 and for PAB it is M30046

If a MTB bacterium is detected (or a sample is already known to be MTB positive), an assay to determine the presence or absence of rifampicin and/or isoniazid resistance in the bacterium is performed. In some embodiments, the antibiotic resistance phase of the assay is performed without the MTB detection phase (e.g., when an individual has already been diagnosed with infection by MTB). In some embodiments, the resistance detection phase of the assay is performed after the MTB detection phase without further sample prep.

In some embodiments, rifampicin resistance is determined based on mutations in rpoB (e.g., including, but not limited to, D516V, H526Y, H526D, or S531L). FIG. 1 shows determination of relevant rpoB mutations.

Figure 2:
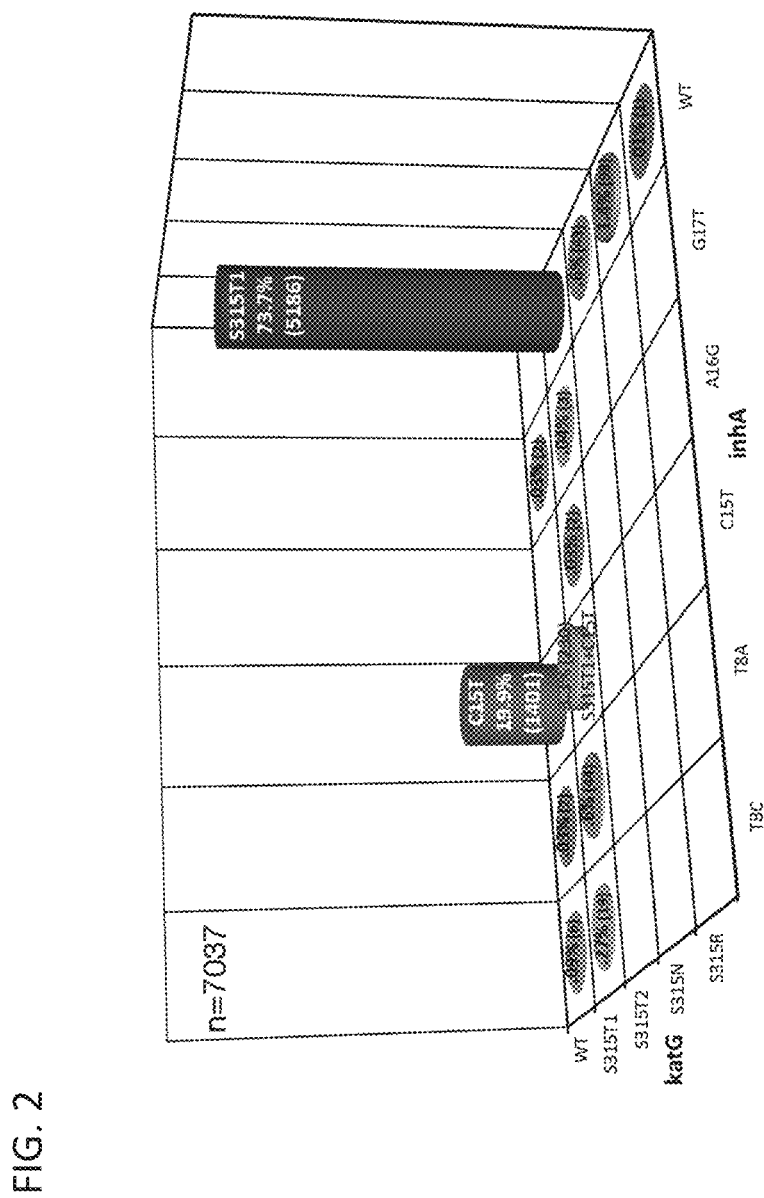
FIG. 2 shows determination of relevant KatG and inhA promoter mutations.
Figure 4C:
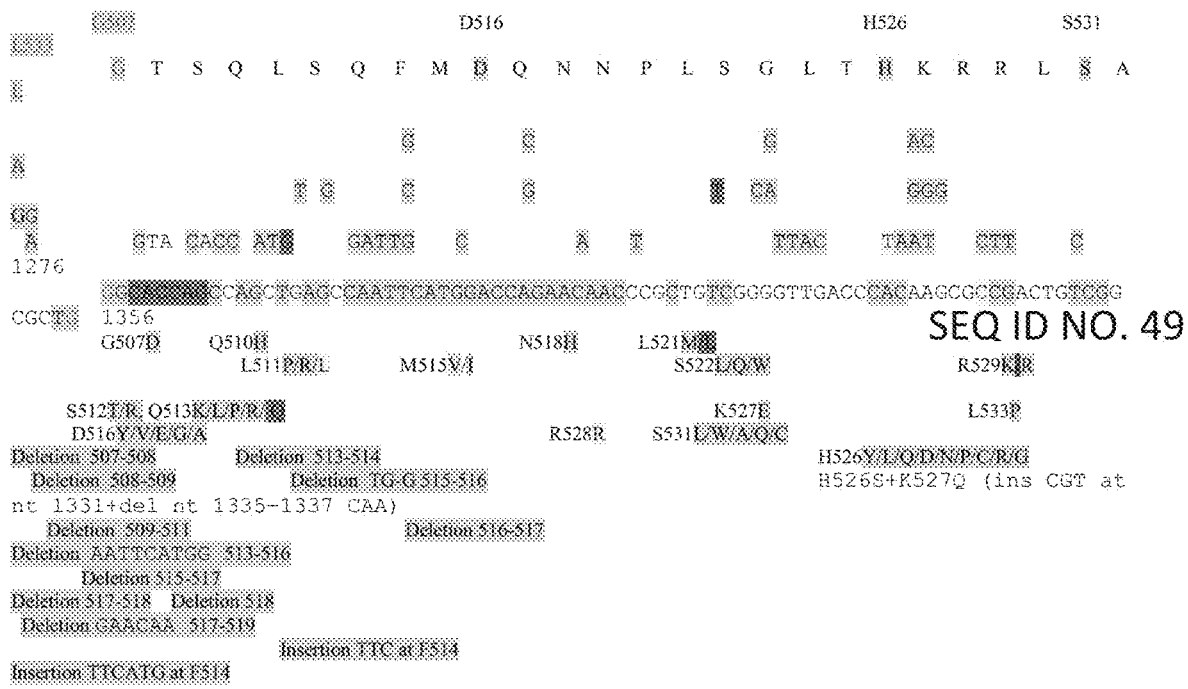
FIGS. 4A through 4Q show nucleotide and amino acid sequences of MTB mutations.

In some embodiments, resistance to isoniazid is determined based on mutations in katG and the inhA promoter (e.g., including, but not limited to, S315T1 in katG and C-15T in the inhA promoter). FIG. 2 shows determination of relevant katG and inhA mutations.

Exemplary primers and probes for identifying the above mutations are shown in SEQ ID NOs: 1-21. The present disclosure is not limited to the primers and probes described in the SEQ ID NOs:1-21. The present disclosure further contemplates sequences comprising, consisting essentially of or consisting of SEQ ID NOs:1-21; variants of SEQ ID NOs:1-21 (e.g., comprising 1, 2, 3, 4, 5, 6, 7, 8, 9, 10 or more nucleotide additions (e.g., to the 3' or 5' end), deletions (e.g., internally or from the 3' or 5' end), or substitutions), polynucleotide sequences that are capable of hybridizing to SEQ ID NOs: 1-21 under conditions of low to high stringency, and the like. In some embodiments, variants comprise non-natural nucleotides. In some embodiments, nucleic acids comprise labels (e.g., those described herein).

In some embodiments, the present disclosure is exemplified with a real time PCR/probe detection assay (RT-PCR) as described in Example 1 below. However, the present disclosure is not limited to RT-PCR. Additional detection methods are described below.

Any suitable sample may be utilized in the compositions and methods disclosed herein. In some embodiments, the sample is sputum, saliva, bronchiolar lavage (BAL), or a. N-acetyl-L-cystine (NALC) sediment of any of the aforementioned samples. In some embodiments, samples are processed prior to assaying (e.g., to isolate bacterial DNA, improve purity, remove materials that may impact assay performance, etc.). In some embodiments, samples are used without further processing.

In some embodiments, sample preparation and assay performance is automated (e.g., using automated sample handling, amplification, and analysis systems). In some embodiments, commercially available systems (e.g., available from Abbott, Abbott Park, Ill.; See e.g., U.S. Pat. No. 8,703,445; herein incorporated by reference in its entirety) are utilized.

In some embodiments, the present disclosure provides software and a computer processor and display screen (e.g., computer, laptop, smart phone, tablet, etc.) for analyzing and displaying data.

In some embodiments, assay components are provided in the form of a system or kit. In some embodiments, kits comprise assay reagents (e.g., nucleic acid primers or probes, buffers, controls, dNTPs, etc.), controls, software, instructions, etc. in some embodiments, reagents are provided in one or more separate containers (e.g., vials, wells, tubes, etc.). For example, in some embodiments, sample preparation reagents, MTB detection reagents, and antibiotic resistance detection mutations are each provided in separate containers.

In some embodiments, MTB detection and mutation analysis assays are nucleic acid detection assays (e.g., amplification, sequencing, hybridization, etc.). Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

In some embodiments, nucleic acid sequencing methods are utilized (e.g., for detection of amplified nucleic acids). In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Binen et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000), Nat. Biotechnol. 18:630-634; U.S. Pat. Nos. 5,695,934; 5,714,330; herein incorporated by reference in their entireties), and the Adessi PCR colony technology (Adessi et al. (2000), Nucleic Acid Res. 28. E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbial., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FIX), Life Technologies/Ion Torrent, the Solexa platform commercialized by illumina, GnuBio, and the Supported Oligonucleotide Ligation and Detection (SOLiD) platform commercialized by Applied Biosystems, Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., Clinical Chem., 55: 641-658, 2009; MacLean et al., Nature Rev. Microbial., 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead. bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al. Nature Rev. Microbiol., 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in Hen Scope by Helicos BioSciences (Voelkerding et al., *Clinical Chem.*, 55: 641-658, 2009; MacLean et al., *Nature Rev. Microbial.*, 7: 287-296; U.S. Pat. Nos. 7,169,560; 7,282,337; 7,482,120; 7,501,245; 6,818,395; 6,911,345; 7.501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced, Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the ion Torrent sequencer is 99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencimg are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, detection methods utilize hybridization assays. Illustrative non-limiting examples of nucleic acid hybridization techniques include, but are not limited to, microarrays including, but not limited to: DNA inicroarrays (e.g., cDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electroChemistry on microelectrode arrays.

Southern and Northern blotting is used to detect specific DNA or RNA sequences, respectively, DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Attachment of fluorophores to nucleic acid probes is well known in the art and may be accomplished by any available means. Fluorophores can be covalently attached to a particular nucleotide, for example, and the labeled nucleotide incorporated into the probe using standard techniques such as nick translation, random priming, PCR labeling, and the like. Alternatively, the fluorophore can be covalently attached via a linker to the deoxycytidine nucleotides of the probe that have been transaminated. Methods for labeling probes are described in U.S. Pat. No. 5,491,224 and Molecular Cytogenetics: Protocols and Applications (2002), Y.-S. Fan, Ed., Chapter 2, "Labeling Fluorescence In Situ Hybridization Probes for Genomic Targets," L. Morrison et al., p. 21-40, Humana Press, both of which are herein incorporated by reference for their descriptions of labeling probes.

Exemplary fluorophores that can be used for labeling probes include TEXAS RED (Molecular Probes, Inc., Eugene, Oreg.), CASCADE blue aectylazide (Molecular Probes, Inc., Eugene, Oreg.), SPECTRUMORANGE™ (Abbott Molecular, Des Plaines, Ill.) and SPECTRUM-GOLD™ (Abbott Molecular).

Examples of fluorophores that can be used in the methods described herein are: 7-amino-4-methylcoumarin-3-acetic acid (AMCA); 5-(and -6)-carboxy-X-rhodamine, lissamine rhodamine B, 5-(and -6)-carboxyfluorescein; fluorescein-5-isothiocyanate (FITC); 7-diethylaminocoumarin-3-carboxylic acid, tetramethyl-rhodamine-5-(and -6)-isothiocyanate, 5-(and -6)-carboxytetramethylrhodamine, 7-hydroxy-coumarin-3-carboxylic acid; 6-[fluorescein 5-(and -6)-carboxamido]hexanoic acid; N-(4,4-difluoro-5,7-dimethyl-4-bora-3a, 4a diaza-3-indacenepropionic acid; eosin-5-isothiocyanate; erythrosine-5-isothiocyanate; 5-(and -6)-carboxyrhodamine 6G; and Cascades blue aectylazide (Molecular Probes, Inc., Eugene, Oreg.).

Probes can be viewed with a fluorescence microscope and an appropriate filter for each fluorophore, or by using dual or triple band-pass filter sets to observe multiple fluorophores. See, e.g., U.S. Pat. No. 5,776,688 to Battier, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytornetty can be used to examine the hybridization pattern of the chromosomal probes.

Probes can also be labeled indirectly, e.g., with biotin or digoxygenin by means well known in the art. However, secondary detection molecules or further processing are then used to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzoate can be used as a substrate for horseradish peroxidase. Fluorescence detection of a hybridized biotin or other indirect labeled probe can be achieved by use of the commercially available tyramide amplification system.

Other agents or dyes can be used in lieu of fluorophores as label-containing moieties. Suitable labels that can be attached to probes include, but are not limited to, radioisotopes, fluorophores, chromophores, mass labels, electron dense particles, magnetic particles, spin labels, molecules that emit luminescence, electrochemically active molecules, enzymes, cofactors, and enzyme substrates. Luminescent agents include, for example, radioluminescent, chemiluminescent, bioluminescent, and phosphorescent label containing moieties. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes may be achieved as described above for ISTI.

In some embodiments, probes are designed to have labels placed at a common interval throughout the nucleic acid (e.g., one label group every 3, 4, 5, 6, 7, 8, 9, 10, 11, or 12).

In some embodiments, a probe library comprises probes with different detectable labels (e.g., different colors of fluorescent signal).

Probes hybridized to target regions may alternatively be visualized by enzymatic reactions of label moieties with suitable substrates for the production of insoluble color products. A biotin-containing probe within a set may be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzidine serves as a substrate for I-IRP.

In embodiments where fluorophore-labeled probes or probe compositions are used, the detection method can involve fluorescence microscopy, flow cytometry, or other means for determining probe hybridization. Any suitable microscopic imaging method may be used in conjunction with the methods of the present disclosure for observing multiple fluorophores. In the case where fluorescence microscopy is employed, hybridized samples may be viewed under light suitable for excitation of each fluorophore and with the use of an appropriate filter or filters. Automated digital imaging systems such as the MetaSystems, BioView or Applied Imaging systems may alternatively be used.

II. Diagnosis, Treatment and Monitoring

Embodiments of the present disclosure provide compositions and methods for diagnosing MTB, determining antibiotic resistance status of MTB infection, and determining and administering a treatment course of action (e.g., for treatment of tuberculosis or other MT infections).

In some embodiments, individuals identified using the methods described herein as antibiotic sensitive are administered standard treatment for tuberculosis (e.g., rifampicin, isoniazid, pyrazinamide, and ethambutol for the first two months, and only rifampicin and isoniazid) for the last four months.

If resistance to one or more antibiotics is identified, alternative treatments are utilized. In some embodiments, individuals identified as having multi-drug resistant MTB using the methods described herein are administered bedaquiline.

In some embodiments, assays for antibiotic resistant MTB described herein are repeated multiple times (e.g., once a month, once every 6 months, once every year, or after several years) to determine if a MTB infection has become resistant during treatment. In some embodiments, assays are repeated after a recurrence of infection by MTB.

The present disclosure contemplates any method capable of receiving, processing, and transmitting the information to and from laboratories conducting the assays, information providers, medical personal, and subjects. For example, in some embodiments of the present disclosure, a sample (e.g., a sputum or BAL sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a sputum sample) and directly send it to a profiling center. Once received by the profiling service, the sample is processed and a profile is produced (e.g., MTB antibiotic resistance profile), specific for the diagnostic or prognostic information desired for the subject.

The profile data is then prepared in a format suitable for interpretation by a treating clinician. For example, rather than providing raw data, the prepared format may represent a diagnosis or risk assessment (e.g., presence of drug resistant MTB) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

EXPERIMENTAL

Example 1

This example describes MTB Detection assays.

The MTB Assay is a qualitative in vitro polymerase chain reaction (PCR) assay for the direct, qualitative detection of the MTB complex. The MTB complex includes eight *Mycobacterium* species: *M. tuberculosis, M. africanum, M. bovis, M. Bovis BCG, M. canettii, M. microti, M. caprae, M. pinnipedii.*

Specimens for the MTB assay, including assay controls, are loaded on an automated. instrument. The DNA is extracted using DNA GPR sample preparation reagents from the Abbott m™ Sample Preparation System$_{DNA}$. The amplification/detection reagents are combined into a mastermix and transferred into a 96-well PCR tray by the m2000sp. Sample eluent is added to the 96-well PCR tray by the m2000sp for the subsequent amplification/detection reaction. Likewise, sample preparation and PCR plate preparation can also be performed manually. The plate is manually sealed and transferred to the m2000rt for the amplification and real-time fluorescence detection reaction. A negative control and a positive control are used with each run. Patient results are automatically reported on the m2000rt workstation. A signal with a valid cycle number less than or equal to a predetermined value is considered positive. A signal with no amplification or with a valid cycle number greater than the predetermined value is considered negative. The negative signal is invalidated when the IC is invalid.

The Abbott RealTime™ MTB Oligonucleotide Reagent (Code 08N15L or 8N15L0099) includes PCR oligo buffer, ultrapure water, dNIPs, one forward primer, one reverse primer and one probe for TB IS6110, one forward primer, one reverse primer, one probe for TB PAB, one forward primer, one reverse primer, and one IC probe for the IC, and ROX Passive Reference Standard. The Oligonucleotide Reagent is filled and assembled into the Abbott RealTime™ MTB Amplification Reagent Kit.

The Activation Reagent (Code 51-503200) contains MgCl$_2$, a co-factor of the TaqGold enzyme. The Activation Reagent is prepared by mixing Magnesium Chloride, Tris, as follows: KCl, PROCLIN 950, Sodium Azide, and ultrapure water. After filtration, the Activation Reagent is filled (Code 5 1-503200FL) and assembled into Abbott RealTime™ MTB Amplification Reagent Kit.

The Enzyme Reagent is prepared by filling AmpliTaq Gold DNA Polymerase (Code 33794) into vials (Code 3379400FL). After filling, it is assembled into the Abbott RealTime™ MTB Amplification Reagent Kit The Abbott RealTime™ MTB controls are used to evaluate nm validity. The control kit consists of positive controls and negative controls. The positive control consists of a dual target PAB/IS6110 plasmid DNA, PROCLIN 950, Sodium Azide and poly dA:dT in TE buffer. The negative control consists of TE buffer, PROCLIN 950, Sodium Azide. The Negative Control (Code 8N15Z0001) and Positive Control (Code 8N15W0001) are filled, labeled and packaged into the Abbott Real Time™ MTB Control Kit.

Sample Preparation Kit

The Abbott Sample Preparation System (List 6K12-24) is comprised of General Purpose Reagents for the isolation of DNA using a non-specific capture chemistry. These reagents are manufactured by Promega Corporation for Abbott Laboratories and are distributed by Abbott Laboratories.

| Real-time MTB Amplification Reagent Kit Formulation | | |
|---|---|---|
| Reagent | Component | Final Reaction Concentration |
| Oligonucleotide | MTB IS6110 (121) Forward Primer | 0.504 uM |
| | MTB IS6110 (121) Reverse Primer | 0.504 uM |
| | MTB PAB abt2 Forward Primer b | 0.504 uM |
| | MTB PAB abt2 Reverse Primer x | 0.504 uM |
| | MTB IS6110 probe 6 | 0.252 uM |
| | MTB PAB probe 1 | 0.202 uM |
| | Internal Control Forward Primer 196 | 0.605 uM |
| | Internal Control Reverse Primer 310 | 0.605 uM |
| | Internal Control probe | 0.504 uM |
| | *Kras 5x PCR Oligo Buffer | 0.504X |
| | ROX Reference | 0.066 uM |
| | dNTPs | 0.706 mM |
| **Activation Reagent | MgCl₂ | 7.086 mM |
| Enzyme | AmpliTaq Gold Polymerase | 14.283 units/reaction |
| ***IC reagent | IC plasmid | Approximately 225 copies/reaction |
| | Negative diluent (TE with poly dA:dT) | MTB IC 8N15Y0001 |

*The KRAS 5X PCR Oligo Buffer contains Tris, EDTA, EGTA, KCl, Sodium Azide and PROCLIN 950.
**The Activation Reagent is in buffer containing Tris, KCl, Sodium Azide and PROCLIN 950.

| Control Kit Formulation | | |
|---|---|---|
| Control | Component | Target Level |
| Negative Control* | TE buffer | NA |
| Positive Control* | TB Plasmid DNA | Target to CN of 30 in FAM Channel |
| | TE buffer | NA |
| | poly dA:dT | NA |

*The Control Reagents contain Sodium Azide and PROCLIN 950.

| Cycling Conditions | | | |
|---|---|---|---|
| Step Number | Number of Cycles | Temperature | Time |
| 1 | 1 | 50 degrees C. | 10 minutes |
| 2 | 1 | 94 degrees C. | 10 minutes |
| 3 | 50 | 94 degrees C. | 35 seconds |
| | | 64 degrees C. | 15 seconds |
| | | 65 degrees C. | 40 seconds |

| Material | Description | SEQ ID NO. |
|---|---|---|
| IS6110 (121) FP | 5' CCT GCG AGC GTA GGC GTC GGT GA 3' | 22 |
| IS6110 (121) RP | 5' CGT CCA GCG CCG CTT CGG ACC A 3' | 23 |
| PAB abt2 FPb | 5' GCA CCT CAA GCT GAA CGG AAA AGT CCT 3' | 24 |
| PAB abt2 RPx | 5' CCG GGG TTG AGC GCA GCG ATC T 3' | 25 |
| IS6110 probe6 | 5' 6-Fam-pdU#AG GpdUG AGG pdUpdC*pdU GpdCpdU ApdCpdC pdC-BHQ1 dT 3' | 26 |
| PAB probe 1 | 5' 6-Fam-pdUApdC pdCAG GGpdC ApdCpdC ApdUpdC AAA-BHQ1 dT 3' | 27 |
| IC FP 196 | 5' CTA CAG CAG AGT TGG CAG CTT CAC TTT C 3' | 28 |
| IC RP 310 | 5' GTC TGG CCT TTC AGC AAG TTT C 3' | 20 |
| Internal Control Probe: | 5' Quasar-GApdC GAG pdUpdUpdC ApdUG AGG GpdCA-BHQ2 dT 3' | 21 |
| Thermostable AmpliTaq ® Gold DNA Polymerase | Refer to MS-33794 for details | | pdU = 5'PROPYNYL dU
*pdC = 5'PROPYNYL dC

Example 2

This example describes an experimental protocol for performing MTB RIF/INH resistance assays.

A. Reagents

Amplification Reagent Kit

The RealTime MTB RIF/INH Resistance Amplification Reagent Kit includes 3 reagent packs and 2 Internal Control bottles (sequences for the described nucleic acids are given below):

(1) Reagent Pack A 1 bottle MTB RIF-1 Resistance Oligonucleotide Reagent A: PCR oligo buffer, ultrapure water, PROCLIN 950, Sodium Azide, dNTPs, IC reverse primer, IC forward primer, IC Probe, rpoB forward primer, rpoB reverse primer, rpoB rPb1 probe, rpoB rPb2 probe, rpoB rPb3, and rpoB Pb4 probe.

1 bottle AmpliTaq Gold DNA Polymerase Enzyme.
1 bottle Activation Reagent.

(2) Reagent Pack B 1 bottle MTB RIF-2 Resistance Oligonucleotide Reagent C: PCR oligo buffer, PROCLIN 950, Sodium Azide, ultrapure water, dNTPs, IC reverse primer, IC forward primer, IC Probe, rpoB forward primer, rpoB Reverse Primer, rpoB Pb5, rpoB Pb6, rpoB rPb7, and rpoB Pb8 probe.

1 bottle AmpliTaq Gold DNA Polymerase Enzyme.
1 bottle Activation Reagent.
(3) Reagent Pack C
1 bottle MTB INH Resistance Oligonucleotide Reagent C: PCR oligo buffer, PROCLIN 950 Sodium Azide, ultrapure water, dNTPs, IC reverse primer, IC forward primer, IC Probe, katG forward primer, katG reverse primer, inhA forward primer, inhA reverse primer, katGrPbwtS315-13b probe, katGrPbm315T1-13b probe, inhA rPbwt-16 probe, and inhA rPbm15T-14 probe.
1 bottle AmpliTaq Gold DNA Polymerase Enzyme.
1 bottle Activation Reagent.
(4) Internal Control 2 bottles MTB Internal Control.

The Oligonucleotide Reagents are filled and assembled into the Abbott RealTime™ MTB RIF/INH Resistance Amplification Reagent Kit.

The Activation Reagent contains $MgCl_2$, a co-factor of the TaqGold enzyme.

The Activation Reagent is prepared by mixing Magnesium Chloride, Tris, KCl, PROCLIN 950, Sodium Azide, and ultrapure water. After filtration, the Activation Reagent is filled and assembled into Abbott Real Time™ MTB RIF/INH Resistance Amplification Reagent Kit The Enzyme Reagent is prepared by filling AmpliTaq Gold DNA Polymerase into vials. After filling, it is assembled into the Abbott RealTime™ MTB RIF/INH Resistance Amplification Reagent Kit.

Control Kit

The Abbott RealTime™ MTB RIF/INH Resistance controls are used to evaluate run validity. The control kit comprises positive controls and negative controls. The positive control consists of plasmid DNA containing five DNA sequences of three target regions (rpoB RIF Resistance-Determining Region (RRDR) wildtype, katG wildtype, inhA Upper Stream Promoter (USP) wildtype, katG mutation, inhA Upper Stream Promoter (USP) mutation), PROCLIN 950, Sodium Azide and poly dA:dT in TE buffer. The negative control consists of TE buffer, PROCLIN 950, Sodium Azide. The Negative Control and Positive Control are filled, labeled and packaged into the Abbott RealTime™ MTB RIF/INH Resistance Control Kit.

Sample Preparation Kit

The Abbott Sample Preparation System (List 6K12-24) is comprised of General Purpose Reagents for the isolation of DNA using a non-specific capture chemistry. These reagents are manufactured by Promega Corporation for Abbott Laboratories and are distributed by Abbott Laboratories.

Real-time MTB Amplification Reagent Kit Formulation

| Reagent | Component | Final Reaction Concentration | Final Oligomix Concentration |
|---|---|---|---|
| Oligonucleotide RIF-1 (Reagent A) and RIF-2 (Reagent B) | MTB R rpoB Forward Primer | .800 µM | 3.789 µM |
| RIF-1 (Reagent A) and RIF-2 (Reagent B) | MTB R rpoB Reverse Primer | .800 µM | 3.789 µM |
| INH (Reagent C) | MTB R katG (Forward Primer | .800 µM | 3.313 µM |
| INH | MTB R katG Reverse Primer | .800 µM | 3.313 µM |
| INH | MTB R inhA Forward Primer | .800 µM | 3.313 µM |
| INH | MTB R inhA Reverse Primer | .800 µM | 3.313 µM |
| RIF-1 | MTB R rpoB Probe 1 | .115 µM | 0.545 µM |
| RIF-1 | MTB R rpoB Probe 2 | .225 µM | 1.066 µM |
| RIF-1 | MTB R rpoB Probe 3 | .090 µM | 0.426 µM |
| RIF-1 | MTB R rpoB Probe 4 | .160 µM | 0.758 µM |
| RIF-2 | MTB R rpoB Probe 5 | .225 µM | 1.066 µM |
| RIF-2 | MTB R rpoB Probe 6 | .225 µM | 1.066 µM |
| RIF-2 | MTB R rpoB Probe 7 | .200 µM | 0.947 µM |
| RIF-2 | MTB R rpoB Probe 8 | .090 µM | 0.426 µM |
| INH | MTB R katG Probe 1 | .225 µM | 0.932 µM |
| INH | MTB R katG Probe 2 | .115 µM | 0.476 µM |
| INH | MTB R inhA Probe 1 | .225 µM | 0.932 µM |
| INH | MTB R inhA Probe 2 | .135 µM | 0.559 µM |
| RIF-1, RIF-2 | Internal Control Forward Primer 196 | .500 µM | 2.368 µM |
| INH | Internal Control Forward Primer 196 | .500 µM | 2.071 µM |
| RIF-1, RIF-2 | Internal Control Reverse Primer 310 (RIF-1 & RIF-2) | .550 µM | 2.605 µM |
| INH | Internal Control Reverse Primer 310 (INH) | .600 µM | 2.485 µM |
| RIF-1, RIF-2 | Internal Control Probe (RIF-1 & RIF-2) | .450 µM | 2.131 µM |
| INH | Internal Control Probe (INH) | .500 µM | 2.071 µM |
| RIF-1, RIF-2, INH | 10X Buffer | 1.10X | 5.209X |
| INH | 10X Buffer | 1.10X | 4.555X |
| RIF-1, and RIF-2 | dNTPs (RIF-1 & RIF-2) | .900 mM | 4.262 mM |
| INH | dNTPs (INH) | .800 mM | 3.313 mM |
| **Activation Reagent (RIF-1 & RIF-2 | $MgCl2$ (RIF-1 & RIF-2) | 9.000 mM | N/A |
| INH | $MgCl2$ (INH) | 8.000 mM | N/A |
| Enzyme (RIF-1 and RIF-2) | AmpliTaq Gold Polymerase (RIF-1 & RIF-2) | 13.000 units/reaction | N/A |
| INH | AmpliTaq Gold Polymerase (INH) | 12.000 units/reaction | N/A |

Real-time MTB Amplification Reagent Kit Formulation

| Reagent | Component | Final Reaction Concentration | Final Oligomix Concentration |
|---|---|---|---|
| ***IC reagent | IC plasmid Negative diluent (TE with poly dA:dT) | Approximately 225 copies/reaction MTB IC 8N15Y0001 | N/A |

*The Oliogomixs (RIF-1(Reagent A), RIF-2 (Reagent B), and INH (Reagent C)) are in PCR Oligo Buffer containing Tris, EDTA, EGTA, KCl, primers, probes, and approximately 0.085% Sodium Azide, and 0.15%) PROCLIN950.
**The Activation Reagent is in buffer containing Tris, KCl, 0.084% Sodium Azide, and 0.15% PROCLIN 950.

Control Kit Formulation

| Control | Component | Target Level |
|---|---|---|
| Negative Control* | TE Buffer | N/A |
| Positive Control** | MTB Resistance wt-15T-315T1 Plasmid DNA | 4E5 copies/mL |
|  | TE Buffer The Table below describes rpoB primers, katG primers, inhA primers, Internal control primers and Internal control probe:

| Material | Description | Mutation Detected | Type of Detection | SEQ ID NO. |
|---|---|---|---|---|
| rpoB F1210-23 | 5'-GAG GCG ATC ACA CCG CAG ACG TT-3' | Primer | N/A | 1 |
| rpoB R1394-21 | 5'-TCC AGC CCG GCA CGC TCA CGT-3' | Primer | N/A | 2 |
| katG F873-22 | 5'-TCC GCT GGA GCA GAT GGG CTT G-3' | Primer | N/A | 3 |
| katG R1000-24 | 5'-CGA GGA AA C TGT TGT CCC ATT TCG-3' | Primer | N/A | 4 |
| inhA F1673379-24 | 5'-ACG TTA CGC TCG TGG ACA TAC CGA-3' | Primer | N/A | 5 |
| inhA R1673492-21 | 5'-ACT GAA CGG GAT ACG AAT GGG-3' | Primer | N/A | 6 |
| IC FP 196 | 5' CTA CAG CAG AGT TGG CAG CTT CAC TTT C 3' | Primer | N/A | 28 |
| IC RP 310 | 5' GTC TGG CCT TTC AGC AAG TTT C 3' | Primer | N/A | 20 |
| Internal Control Probe: | 5' Qmsar-GANC GAG pdUpdUpdC ApdUG AGG GpdCA-BHQ2 dT 3' | Internal Control | Positive | 21 |

The Table below describes mutation coverage by each probe.

| Material | Description | Mutation Coverage | Type of Detection | SEQ ID NO. |
|---|---|---|---|---|
| rpoB rPb1 (1288-13) | 5'-CFR 610-GCT GGC TGG TGC C-MGB-DQ-3' | Amino acids 507-511 e.g., Q510E | Negative | 1 |
| rpoB rPb2 (1309-15) | 5'-NED-TCT GGT CCA TGA ATT-MGB-DQ-3' | Amino acids 513-518 e.g, D516V, D516Y | Negative | 2 |
| rpoB rPb3 (1329-13) | 5'-VIC-CAA CCC CGA CAG C-MGB-DQ-3' | Amino acids 520-524 e.g., L521M | Negative | 9 |
| rpoB Pb4 (1345-13) | 5'-6FAM-CTG TCG GCG CTG G-MGB-DQ-3' | Amino acids 530-533 e.g., S531L, S531W | Negative | 10 |
| rpoB Pb5 (1285-14) | 5'-CFR610-CAG CTG AGC CAA TT-MGB-DQ-3' | Amino acids 510-514 e.g., L511P | Negative | 11 |
| rpoB Pb6 (1307-14) | 5'-NED-AGA ACA ACC CCC TG-MGB-DQ-3' | Amino acids 517-521 e.g., N5181 | Negative | 12 |
| rpoB rPb7 (1338-14) | 5'-VIC-CTT GIG GGT CAA CC-MGB-DQ-3' | Amino acids 523-527 e.g., H526Y, H526D | Negative | 13 |
| rpoB Pb8 (1337-14) | 5'-6FAM-AGC GCC GAC TGT CG-MGB-DQ-3' | Amino acids 527-531 e.g., L530M | Negative | 14 |

| Material | Description | Mutation Coverage | Type of Detection | SEQ ID NO. |
|---|---|---|---|---|
| katGrPbwtS315-13b | 5'-NED-ATG CCG CTG GTG A-MGB-DQ-3' | 315T1, other mutations (e.g., 315T2, 315T3, 315N, 315I, 315R1, 315R2, 315G, 315L) | Negative | 15 |
| katGrPbm315T1-13b | 5'-6FAM-ATG CCG GTG GTG A-MGB-DQ-3' | 315T1 | Positive | 16 |
| inhA rPbwt-16 | 5'-CFR610-ACA ACC TAT CGT CTC G-MGB-DQ-3' | C-15T, other mutations (e.g., G17T, A16G, T8C, T8A, T8G) | Negative | 17 |
| inhA rPbm15T-14 | 5'-VIC-CAA CCT ATC ATC TC-MGB-DQ-3' | C-15T | Positive | 18 |

Below are the genBank accession numbers of TB Drug Resistance Mutation Database References for primers and probes/mutations of rpoB, katG, and inhA upper stream promoter.

```
rpoB 171210-23:
                                SEQ ID NO. 1
5'-GAG GCG ATC ACA CCG CAG ACG TT-3'
(gb/AL123456) RIF-1 Vial and RIF-2
Vial rpoB R1394-21:
                                SEQ ID NO. 2
5'-TCC AGC CCG GCA CGC TCA CGT-3
2(gib/AL1234561 RIF-1 Vial and RIF-2
Vial katG F873-22:
                                SEQ ID NO. 3
5'-TCC GCT GGA GCA GAT GGG CTT G-3'
(gb/AL123456) INH Vial katG R1000-24:
                                SEQ ID NO. 4
5'-CGA GGA AAC TGT TGT CCC ATT TCG-3'
(gb/AL123456) INH Vial inhA F1673379-24:
                                SEQ ID NO. 5
5'-ACG TTA CGC TCG TGG ACA TAC CGA-3'
(gb/AL123456) INH Vial inhA R1673492-21:
                                SEQ ID NO. 6
5'-ACT GAA CGG GAT ACG AAT GGG-3'
(gb/AL123456) INH Vial rpoB rPb1(rPb1288-13(1h)):
                                SEQ ID NO. 7
5'-CalFluoRed 610-GCTGGCTGGTGCC-MGB-3'
(2b/AL123456, Rv0667) RIF-1 Vial rpoB rPb2 (rPh1309-15(20):
                                SEQ ID NO. 8
5'-NED-TCTGGTCCATGAATT-MGB-3'
(gb/AL123456, Rv0667) RIF-1 Vial rpoB rPb3(rPb1329-13(3S)):
                                SEQ ID NO. 9
5'-VIC-CAACCCCGACAGC-MGB-3'
(gb/AL123456, Rv0667) RIF-1 Vial rpoB Pb4(Pb1345-131410):
                                SEQ ID NO. 10
5'-6FAM-CTGTCGGCGCTGG-MGB-3'
(gb/AL123456, Rv0667) RIF-1 Vial rpoB Pb5(Pb1285-14(5a)):
                                SEQ ID NO. 11
5'-CalfluoRed 610-CAGCTGAGCCAATT-MG9-3'
(gb/AL123456, Rv0667) RIF-2 Vial rpoB Pb6(Pb1307-14(6d)):
                                SEQ ID NO. 12
5'-NED-AGAACAACCCGCTG-MGB-3'
(gb/AL123456, Rv0667) RIF-2 Vial rpoB rPb7(rPb1338-14(7h):
                                SEQ ID NO. 13
5'-VIC-CTTGTGGGTCAACC-MGB-3'
(gb/AL123456, Rv0667) RIF-2 Vial rpoB Pb8(Pb1337-14(8J)):
                                SEQ ID NO. 14
5'-6FAM-AGCGCCGACIGTCG-MGB-3
(gb/AL123456, Rv0667) R1F-2 Vial
```

Representative Mutations Covered by rpoB Probes:

```
rpoB rPb1(rPb1288-13(1h)):
                                SEQ ID NO. 7
5'-CalFluoRed 610-GCTGGCTGGTGCC-MGB-3'
(Amino acids 507-511; e.g., Q510E, gb/EF628328)

rpoB rPb2 (rPb1309-15(2c)):
                                SEQ ID NO. 8
5'-NED-TCTGGTCCATGAATT-MGB-3'
(Amino acids 513-518; e.g, D516V, gb/JF269609;
D516Y, gb/HQ286625)

rpoB rPb3(rPb1329-13(3S)):
                                SEQ ID NO. 9
5'-VIC-CAACCCCGACAGC-MGB-3'
(Amino acids 520-524; e.g., L521M, gb/AB711174)

rpoB Pb4 (Pb1345-13(4k)):
                                SEQ ID NO. 10
5'-6FAM-CTGTCGGCGCTGG-MGB-3'
(Amino acids 530-533; e.g., S53IL,
gb/HM179030, S531W, gb/GU904014)
```

-continued rpoB Pb5(Pb1285-14(5a)):
SEQ ID NO. 11
5'-CalFluoRed 610-CAGCTGAGCCAATT-MGB-3'
(Amino acids 510-514; e.g., L511P, gb/PQ414016)

rpoB Pb6(Pb1307-14(6d)):
SEQ ID NO. 12
5'-NED-AGAACAACCCGCTG-MGB-3
(Amino acids 517-521; e.g., N518I, gb/AB711171)

rpoB rPb7(rPb1338-14(7h)):
SEQ ID NO. 13
5'-VIC-MGTGGGTCAACC-MGB-3'
(Amino acids 523-527; e.g., H526Y, gb/AY271365; H526D, gb/HQ844251)

rpoB Pb8(Pb1337-14(8J)):
SEQ ID NO. 14
5'-6FAM-AGCGCCGACTGTCG-MGB-3'
(Amino acids 527-531; e.g., L530M, gb/DQ205438)

Representative Mutations Covered by katG Probes:

SEQ ID NO. 29

INH Vial  NED  TCACCAGCGGCAT:katGrPb950  wt315-13b  (gb/AL123456, Rv1908c)

SEQ ID NO. 30

INH Vial  FAM  TCACCACCGGCAT:katG rPb950  mt315T1-13b  (gb/DQ056354)
                     ACA                  mt315T2      (gb/U41309)
                     ACG                  mt315T3 (TBDReaMDB:Gagneux S PLOS Path 2006)
                     AAC                  mt315N       (gb/DQ056356)
                     ATC                  mt315I       (gb/AF314112)
                     AGA                  mt315R1 (TBDReaMDB:Lipin MY CMI 2007)
                     CGC                  mt315R2 (TBDReaMDB:Haas WA AAC 1997)
                     AGG                  mt315R3      (gb/EU884628)
                     GGC                  mt315G       (gb/EU884620)
                     CTA                  mt315L (TBDReaMDB:Marttila HJ AAC 1996)

Representative Mutations Covered by inhA Upper Stream Promoter (USP) Probes:

SEQ ID NO. 31

INH Vial  CalFluoRed  610  CGAGACGATAGGTTGT inhA rPbwt-16  (gb/AL123456)

SEQ ID NO. 32

INH Vial         VIC   GAGATGATAGGTTG  inhA rPbm15T-14 (gb/FM173198)
                              T              rPbm17T        (gb/AY192027)
                              G              rPbm16G (Ramaswamy S Mussser JM Tubercle ling Dis 1998)
                              C              rPbm8C         (TBDReaMDB:Baker LV AAC 2005)
                              A              rPbm8A         (gb/CP001658)
                              G              rPbm8G         (gb/FM173199)

B. Assay Protocol

Specimens for the Abbott RealTime™ MTB RIF/INH Resistance assay, including assay controls, are loaded on the m2000sp instrument. The DNA is extracted using DNA sample preparation reagents from the Abbott m™ Sample Preparation SystemDNA. The amplification/detection reagents are combined into a mastermix and transferred into a 96-well PCR tray by the m2000sp, Sample eluent is added to the 96-well PCR tray by the m2000sp for the subsequent amplification/detection reaction. Likewise, sample preparation and PCR plate preparation can also be performed manually. The plate is manually sealed and transferred to the m2000rt for the amplification and real-time fluorescence detection reaction. A negative control and a positive control are required with each run. Patient results are automatically reported on the m2000rt workstation:

Cycling Conditions:

| Step Number | Number of Cycles | Temperature | Time |
|---|---|---|---|
| 1 | 1 | 50 degrees C. | 10 minutes |
| 2 | 1 | 94 degrees C. | 10 minutes |
| 3 | 50 | 94 degrees C. | 35 seconds |
|  |  | 64 degrees C. | 15 seconds |
|  |  | 65 degrees C. | 40 seconds |

C. Results

FIG. 3 shows results of rifampicin and isoniazid detection for drug sensitive (FIG. 3A) and drug resistant (FIG. 3B) bacteria.

In addition, 70 purified clinical MTB genomic DNA samples from Dr. Kreiswirth (an expert in TB drug resistance) were tested. All 70 genomic DNA samples had DST results and sequencing results. The following mutations were detected in the clinical samples: rpoB: L533P, S531L, S531W, S531F, H526Y, H526D, H526R, H526N, D516V, D516Y, D516G, D516A, H512R, L511P, and insertion 514-515. katG: S315T1, S315N, and S315I. inh A upper steam promoter: C15T and T8A.

Results are shown below:

| Assay | RIF Sensitivity (%) | RIF Specificity (%) | INH Sensitivity (%) | INH Specificity (%) |
|---|---|---|---|---|
| AM MTB RIF/INH | 84.4 (38/45) | 96.0 (24/25) | 91.5 (43/47) | 95.7 (22/23) |

290 MTB cultured clinical isolates obtained from Bangladesh were also assayed. Results are shown below.

| Assay | RIF Sensitivity (%) | RIF Specificity (%) | INH Sensitivity (%) | INH Specificity (%) |
|---|---|---|---|---|
| AM MTB RIF/INH | 86.2 (25/29) | 100.0 (260/260) | 86.1-91.7 (31/36-33*/36) | 100.0 (253/253) |

All 290 cultured clinical isolates had DST results. These cultured clinical isolates (heat-inactivated) were treated with AM Inactivation Reagent (IR) then processed through m2000sp sample preparation All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

---

What is claimed is:

1. A kit comprising
primer pairs consisting of SEQ ID NOS: 22-23, SEQ ID NOS: 24-25, SEQ ID NOS: 1-2, SEQ ID NOS: 3-4 and SEQ ID NOS: 5-6 and probes consisting of SEQ ID NO: 26, SEQ ID NO: 27, SEQ ID NOS: 7-14, SEQ ID NOS: 15-16 and SEQ ID NOS: 17-18.

2. The kit of claim 1, further comprising a control nucleic acid.

3. The kit of claim 1, wherein said control nucleic acid is a negative control nucleic acid.

4. The kit of claim 1, wherein said control nucleic acid is a positive control nucleic acid.

5. The kit of claim 1, further comprising an internal forward primer and an internal reverse primer.

6. The kit of claim 1, further comprising an internal control probe.

7. The kit of claim 1, further comprising one or more dinucleotide triphosphates (dNTPs).

8. The kit of claim 1, further comprising poly dA:dT.

9. The kit of claim 1, further comprising Tris-EDTA (TE) buffer.

10. The kit of claim 1, further comprising one or more sample preparation reagents.

11. The kit of claim 1, further comprising a polymerase.

12. The kit of claim 1, further comprising ethylenediaminetetraacetic acid (EDTA).

13. The kit of claim 1, further comprising ethylene glycol-bis(6-aminoethyl ether)-N,N,N',N'-tetraacetic acid (EGTA).

14. The kit of claim 1, further comprising a 96-well PCR tray.

15. The kit of claim 1, further comprising one or more of MgCl$_2$, Tris, KCl, PROCLIN 950, sodium azide and ultrapure water.

* * * * *

SEQUENCE LISTING

```
<160> NUMBER OF SEQ ID NOS: 53

<210> SEQ ID NO 1
<211> LENGTH: 23
<212> TYPE: DNA
<213> ORGANISM: Artificial
<220> FEATURE:
<223> OTHER INFORMATION: Synthetic

<400> SEQUENCE: 1
gaggcgatca caccgcagac gtt                                           23

<210> SEQ ID NO 2
<211> LENGTH: 21
<212> TYPE: DNA
<213> ORGANISM: Artificial
<220> FEATURE:
<223> OTHER INFORMATION: Synthetic

<400> SEQUENCE: 2
tccagcccgg cacgctcacg t                                             21

<210> SEQ ID NO 3
<211> LENGTH: 22
<212> TYPE: DNA
<213> ORGANISM: Artificial
<220> FEATURE:
<223> OTHER INFORMATION: Synthetic
```

```
<400> SEQUENCE: 3
tccgctggag cagatgggct tg                                           22

<210> SEQ ID NO 4
<211> LENGTH: 24
<212> TYPE: DNA
<213> ORGANISM: Artificial
<220> FEATURE:
<223> OTHER INFORMATION: Synthetic

<400> SEQUENCE: 4
cgaggaaact gttgtcccat ttcg                                         24

<210> SEQ ID NO 5
<211> LENGTH: 24
<212> TYPE: DNA
<213> ORGANISM: Artificial
<220> FEATURE:
<223> OTHER INFORMATION: Synthetic

<400> SEQUENCE: 5
acgttacgct cgtggacata ccga                                         24

<210> SEQ ID NO 6
<211> LENGTH: 21
<212> TYPE: DNA
<213> ORGANISM: Artificial
<220> FEATURE:
<223> OTHER INFORMATION: Synthetic

<400> SEQUENCE: 6
actgaacggg atacgaatgg g                                            21

<210> SEQ ID NO 7
<211> LENGTH: 13
<212> TYPE: DNA
<213> ORGANISM: Artificial
<220> FEATURE:
<223> OTHER INFORMATION: Synthetic

<400> SEQUENCE: 7
gctggctggt gcc                                                     13

<210> SEQ ID NO 8
<211> LENGTH: 15
<212> TYPE: DNA
<213> ORGANISM: Artificial
<220> FEATURE:
<223> OTHER INFORMATION: Synthetic

<400> SEQUENCE: 8
tctggtccat gaatt                                                   15

<210> SEQ ID NO 9
<211> LENGTH: 13
<212> TYPE: DNA
<213> ORGANISM: Artificial
<220> FEATURE:
<223> OTHER INFORMATION: Synthetic

<400> SEQUENCE: 9
caaccccgac agc                                                     13

<210> SEQ ID NO 10
<211> LENGTH: 13
```

```
<212> TYPE: DNA
<213> ORGANISM: Artificial
<220> FEATURE:
<223> OTHER INFORMATION: Synthetic

<400> SEQUENCE: 10
ctgtcggcgc tgg                                                        13

<210> SEQ ID NO 11
<211> LENGTH: 14
<212> TYPE: DNA
<213> ORGANISM: Artificial
<220> FEATURE:
<223> OTHER INFORMATION: Synthetic

<400> SEQUENCE: 11
cagctgagcc aatt                                                       14

<210> SEQ ID NO 12
<211> LENGTH: 14
<212> TYPE: DNA
<213> ORGANISM: Artificial
<220> FEATURE:
<223> OTHER INFORMATION: Synthetic

<400> SEQUENCE: 12
agaacaaccc gctg                                                       14

<210> SEQ ID NO 13
<211> LENGTH: 14
<212> TYPE: DNA
<213> ORGANISM: Artificial
<220> FEATURE:
<223> OTHER INFORMATION: Synthetic

<400> SEQUENCE: 13
cttgtgggtc aacc                                                       14

<210> SEQ ID NO 14
<211> LENGTH: 14
<212> TYPE: DNA
<213> ORGANISM: Artificial
<220> FEATURE:
<223> OTHER INFORMATION: Synthetic

<400> SEQUENCE: 14
agcgccgact gtcg                                                       14

<210> SEQ ID NO 15
<211> LENGTH: 13
<212> TYPE: DNA
<213> ORGANISM: Artificial
<220> FEATURE:
<223> OTHER INFORMATION: Synthetic

<400> SEQUENCE: 15
atgccgctgg tga                                                        13

<210> SEQ ID NO 16
<211> LENGTH: 13
<212> TYPE: DNA
<213> ORGANISM: Artificial
<220> FEATURE:
<223> OTHER INFORMATION: Synthetic

<400> SEQUENCE: 16
```

```
atgccggtgg tga                                                          13
```

<210> SEQ ID NO 17
<211> LENGTH: 16
<212> TYPE: DNA
<213> ORGANISM: Artificial
<220> FEATURE:
<223> OTHER INFORMATION: Synthetic

<400> SEQUENCE: 17

```
acaacctatc gtctcg                                                       16
```

<210> SEQ ID NO 18
<211> LENGTH: 14
<212> TYPE: DNA
<213> ORGANISM: Artificial
<220> FEATURE:
<223> OTHER INFORMATION: Synthetic

<400> SEQUENCE: 18

```
caacctatca tctc                                                         14
```

<210> SEQ ID NO 19
<211> LENGTH: 25
<212> TYPE: DNA
<213> ORGANISM: Artificial
<220> FEATURE:
<223> OTHER INFORMATION: Synthetic

<400> SEQUENCE: 19

```
cagcagagtt ggcagcttca ctttc                                             25
```

<210> SEQ ID NO 20
<211> LENGTH: 22
<212> TYPE: DNA
<213> ORGANISM: Artificial
<220> FEATURE:
<223> OTHER INFORMATION: Synthetic

<400> SEQUENCE: 20

```
gtctggcctt tcagcaagtt tc                                                22
```

<210> SEQ ID NO 21
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 5'PROPYNYL dC
<220> FEATURE:
<221> NAME/KEY: misc_feature
<222> LOCATION: (7)..(7)
<223> OTHER INFORMATION: 5'PROPYNYL dU
<220> FEATURE:
<221> NAME/KEY: misc_feature
<222> LOCATION: (8)..(8)
<223> OTHER INFORMATION: 5'PROPYNYL dU
<220> FEATURE:
<221> NAME/KEY: misc_feature
<222> LOCATION: (9)..(9)
<223> OTHER INFORMATION: 5'PROPYNYL dC
<220> FEATURE:
<221> NAME/KEY: misc_feature
<222> LOCATION: (11)..(11)
<223> OTHER INFORMATION: 5'PROPYNYL dU
<220> FEATURE:
<221> NAME/KEY: misc_feature
<222> LOCATION: (17)..(17)
<223> OTHER INFORMATION: 5'PROPYNYL dC

<400> SEQUENCE: 21
gangagnnna ngagggna                                                    18

<210> SEQ ID NO 22
<211> LENGTH: 23
<212> TYPE: DNA
<213> ORGANISM: Artificial
<220> FEATURE:
<223> OTHER INFORMATION: Synthetic

<400> SEQUENCE: 22
cctgcgagcg taggcgtcgg tga                                              23

<210> SEQ ID NO 23
<211> LENGTH: 22
<212> TYPE: DNA
<213> ORGANISM: Artificial
<220> FEATURE:
<223> OTHER INFORMATION: Synthetic

<400> SEQUENCE: 23
cgtccagcgc cgcttcggac ca                                               22

<210> SEQ ID NO 24
<211> LENGTH: 27
<212> TYPE: DNA
<213> ORGANISM: Artificial
<220> FEATURE:
<223> OTHER INFORMATION: Synthetic

<400> SEQUENCE: 24
gcacctcaag ctgaacggaa aagtcct                                          27

<210> SEQ ID NO 25
<211> LENGTH: 22
<212> TYPE: DNA
<213> ORGANISM: Artificial
<220> FEATURE:
<223> OTHER INFORMATION: Synthetic

<400> SEQUENCE: 25
ccggggttga gcgcagcgat ct                                               22

<210> SEQ ID NO 26
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'PROPYNYL dU
<220> FEATURE:
<221> NAME/KEY: misc_feature
<222> LOCATION: (5)..(5)
<223> OTHER INFORMATION: 5'PROPYNYL dU
<220> FEATURE:
<221> NAME/KEY: misc_feature
<222> LOCATION: (10)..(10)
<223> OTHER INFORMATION: 5'PROPYNYL dU
<220> FEATURE:
<221> NAME/KEY: misc_feature
<222> LOCATION: (11)..(11)
<223> OTHER INFORMATION: 5'PROPYNYL dC
<220> FEATURE:

```
<221> NAME/KEY: misc_feature
<222> LOCATION: (12)..(12)
<223> OTHER INFORMATION: 5'PROPYNYL dU
<220> FEATURE:
<221> NAME/KEY: misc_feature
<222> LOCATION: (14)..(14)
<223> OTHER INFORMATION: 5'PROPYNYL dC
<220> FEATURE:
<221> NAME/KEY: misc_feature
<222> LOCATION: (15)..(15)
<223> OTHER INFORMATION: 5'PROPYNYL dU
<220> FEATURE:
<221> NAME/KEY: misc_feature
<222> LOCATION: (17)..(19)
<223> OTHER INFORMATION: 5'PROPYNYL dC

<400> SEQUENCE: 26
naggngaggn nngnnannn                                                19

<210> SEQ ID NO 27
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'PROPYNYL dU
<220> FEATURE:
<221> NAME/KEY: misc_feature
<222> LOCATION: (3)..(4)
<223> OTHER INFORMATION: 5'PROPYNYL dC
<220> FEATURE:
<221> NAME/KEY: misc_feature
<222> LOCATION: (9)..(9)
<223> OTHER INFORMATION: 5'PROPYNYL dC
<220> FEATURE:
<221> NAME/KEY: misc_feature
<222> LOCATION: (11)..(12)
<223> OTHER INFORMATION: 5'PROPYNYL dC
<220> FEATURE:
<221> NAME/KEY: misc_feature
<222> LOCATION: (14)..(14)
<223> OTHER INFORMATION: 5'PROPYNYL dU
<220> FEATURE:
<221> NAME/KEY: misc_feature
<222> LOCATION: (15)..(15)
<223> OTHER INFORMATION: 5'PROPYNYL dC

<400> SEQUENCE: 27
nannagggna nnannaaa                                                 18

<210> SEQ ID NO 28
<211> LENGTH: 28
<212> TYPE: DNA
<213> ORGANISM: Artificial
<220> FEATURE:
<223> OTHER INFORMATION: Synthetic

<400> SEQUENCE: 28
ctacagcaga gttggcagct tcactttc                                      28

<210> SEQ ID NO 29
<211> LENGTH: 13
<212> TYPE: DNA
<213> ORGANISM: Artificial
<220> FEATURE:
<223> OTHER INFORMATION: Synthetic

<400> SEQUENCE: 29
tcaccagcgg cat                                                      13
```

```
<210> SEQ ID NO 30
<211> LENGTH: 13
<212> TYPE: DNA
<213> ORGANISM: Artificial
<220> FEATURE:
<223> OTHER INFORMATION: Synthetic

<400> SEQUENCE: 30
tcaccaccgg cat                                                          13

<210> SEQ ID NO 31
<211> LENGTH: 16
<212> TYPE: DNA
<213> ORGANISM: Artificial
<220> FEATURE:
<223> OTHER INFORMATION: Synthetic

<400> SEQUENCE: 31
cgagacgata ggttgt                                                       16

<210> SEQ ID NO 32
<211> LENGTH: 14
<212> TYPE: DNA
<213> ORGANISM: Artificial
<220> FEATURE:
<223> OTHER INFORMATION: Synthetic

<400> SEQUENCE: 32
gagatgatag gttg                                                         14

<210> SEQ ID NO 33
<211> LENGTH: 120
<212> TYPE: DNA
<213> ORGANISM: Artificial
<220> FEATURE:
<223> OTHER INFORMATION: Synthetic

<400> SEQUENCE: 33
gaggtggagt acgtgccctc gtctgaggtg gactacatgg acgtctcgcc ccgccagatg       60
gtgtcggtgg ccaccgcgat gattcccttc ctggagcacg acgacgccaa ccgtgccctc     120

<210> SEQ ID NO 34
<211> LENGTH: 120
<212> TYPE: DNA
<213> ORGANISM: Artificial
<220> FEATURE:
<223> OTHER INFORMATION: Synthetic

<400> SEQUENCE: 34 atggggggcaa acatgcagcg ccaggcggtg ccgctggtcc gtagcgaggc cccgctggtg      60
ggcaccggga tggagctgcg cgcggcgatc gacgccggcg acgtcgtcgt cgccgaagaa    120

<210> SEQ ID NO 35
<211> LENGTH: 120
<212> TYPE: DNA
<213> ORGANISM: Artificial
<220> FEATURE:
<223> OTHER INFORMATION: Synthetic

<400> SEQUENCE: 35
agcggcgtca tcgaggaggt gtcggccgac tacatcactg tgatgcacga caacggcacc      60
cggcgtacct accggatgcg caagtttgcc cggtccaacc acggcacttg cgccaaccag    120
```

<210> SEQ ID NO 36
<211> LENGTH: 120
<212> TYPE: DNA
<213> ORGANISM: Artificial
<220> FEATURE:
<223> OTHER INFORMATION: Synthetic

<400> SEQUENCE: 36
tgccccatcg tggacgcggg cgaccgagtc gaggccggtc aggtgatcgc cgacggtccc    60
tgtactgacg acggcgagat ggcgctgggc aagaacctgc tggtggccat catgccgtgg   120

<210> SEQ ID NO 37
<211> LENGTH: 120
<212> TYPE: DNA
<213> ORGANISM: Artificial
<220> FEATURE:
<223> OTHER INFORMATION: Synthetic

<400> SEQUENCE: 37
gagggccaca actacgagga cgcgatcatc ctgtccaacc gcctggtcga agaggacgtg    60
ctcacctcga tccacatcga ggagcatgag atcgatgctc gcgacaccaa gctgggtgcg   120

<210> SEQ ID NO 38
<211> LENGTH: 120
<212> TYPE: DNA
<213> ORGANISM: Artificial
<220> FEATURE:
<223> OTHER INFORMATION: Synthetic

<400> SEQUENCE: 38
gaggagatca cccgcgacat cccgaacatc tccgacgagg tgctcgccga cctggatgag    60
cggggcatcg tgcgcatcgg tgccgaggtt cgcgacgggg acatcctggt cggcaaggtc   120

<210> SEQ ID NO 39
<211> LENGTH: 120
<212> TYPE: DNA
<213> ORGANISM: Artificial
<220> FEATURE:
<223> OTHER INFORMATION: Synthetic

<400> SEQUENCE: 39
accccgaagg gtgagaccga gctgacgccg gaggagcggc tgctgcgtgc catcttcggt    60
gagaaggccc gcgaggtgcg cgacacttcg ctgaaggtgc cgcacggcga atccggcaag   120

<210> SEQ ID NO 40
<211> LENGTH: 120
<212> TYPE: DNA
<213> ORGANISM: Artificial
<220> FEATURE:
<223> OTHER INFORMATION: Synthetic

<400> SEQUENCE: 40
gtgatcggca ttcgggtgtt ttcccgcgag gacgaggacg agttgccggc cggtgtcaac    60
gagctggtgc gtgtgtatgt ggctcagaaa cgcaagatct ccgacggtga caagctggcc   120

<210> SEQ ID NO 41
<211> LENGTH: 120
<212> TYPE: DNA
<213> ORGANISM: Artificial
<220> FEATURE:
<223> OTHER INFORMATION: Synthetic

<400> SEQUENCE: 41

```
ggccggcacg gcaacaaggg cgtgatcggc aagatcctgc cggttgagga catgccgttc    60
cttgccgacg gcaccccggt ggacattatt ttgaacaccc acggcgtgcc gcgacggatg   120

<210> SEQ ID NO 42
<211> LENGTH: 120
<212> TYPE: DNA
<213> ORGANISM: Artificial
<220> FEATURE:
<223> OTHER INFORMATION: Synthetic

<400> SEQUENCE: 42
aacatcggcc agattttgga gacccacctg ggttggtgtg cccacagcgg ctggaaggtc    60
gacgccgcca aggggttcc ggactgggcc gccaggctgc cgacgaact gctcgaggcg   120

<210> SEQ ID NO 43
<211> LENGTH: 120
<212> TYPE: DNA
<213> ORGANISM: Artificial
<220> FEATURE:
<223> OTHER INFORMATION: Synthetic

<400> SEQUENCE: 43
cagccgaacg ccattgtgtc gacgccggtg ttcgacggcg cccaggaggc cgagctgcag    60
ggcctgttgt cgtgcacgct gcccaaccgc gacggtgacg tgctggtcga cgccgacggc   120

<210> SEQ ID NO 44
<211> LENGTH: 120
<212> TYPE: DNA
<213> ORGANISM: Artificial
<220> FEATURE:
<223> OTHER INFORMATION: Synthetic

<400> SEQUENCE: 44
aaggccatgc tcttcgacgg gcgcagcggc gagccgttcc cgtacccggt cacggttggc    60
tacatgtaca tcatgaagct gcaccacctg gtggacgaca agatccacgc ccgctccacc   120

<210> SEQ ID NO 45
<211> LENGTH: 120
<212> TYPE: DNA
<213> ORGANISM: Artificial
<220> FEATURE:
<223> OTHER INFORMATION: Synthetic

<400> SEQUENCE: 45
gggccgtact cgatgatcac ccagcagccg ctgggcggta aggcgcagtt cggtggccag    60
cggttcgggg agatggagtg ctgggccatg caggcctacg gtgctgccta caccctgcag   120

<210> SEQ ID NO 46
<211> LENGTH: 120
<212> TYPE: DNA
<213> ORGANISM: Artificial
<220> FEATURE:
<223> OTHER INFORMATION: Synthetic

<400> SEQUENCE: 46
gagctgttga ccatcaagtc cgatgacacc gtcggccgcg tcaaggtgta cgaggcgatc    60
gtcaagggtg agaacatccc ggagccgggc atccccgagt cgttcaaggt gctgctcaaa   120

<210> SEQ ID NO 47
<211> LENGTH: 120
<212> TYPE: DNA
```

```
<213> ORGANISM: Artificial
<220> FEATURE:
<223> OTHER INFORMATION: Synthetic

<400> SEQUENCE: 47
gaactgcagt cgctgtgcct caacgtcgag gtgctatcga gtgacggtgc ggcgatcgaa    60
ctgcgcgaag gtgaggacga ggacctggag cgggccgcgg ccaacctggg aatcaatctg   120

<210> SEQ ID NO 48
<211> LENGTH: 39
<212> TYPE: DNA
<213> ORGANISM: Artificial
<220> FEATURE:
<223> OTHER INFORMATION: Synthetic

<400> SEQUENCE: 48
tcccgcaacg aatccgcaag tgtcgaggat cttgcgtaa                            39

<210> SEQ ID NO 49
<211> LENGTH: 81
<212> TYPE: DNA
<213> ORGANISM: Artificial
<220> FEATURE:
<223> OTHER INFORMATION: Synthetic

<400> SEQUENCE: 49
ggcaccagcc agctgagcca attcatggac cagaacaacc cgctgtcggg gttgacccac    60
aagcgccgac tgtcggcgct g                                              81

<210> SEQ ID NO 50
<211> LENGTH: 113
<212> TYPE: DNA
<213> ORGANISM: Artificial
<220> FEATURE:
<223> OTHER INFORMATION: Synthetic

<400> SEQUENCE: 50
tggaggcgat cacaccgcag acgttgatca acatccggcc ggtggtcgcc gcgatcaagg    60
agttcttcgg caccagccag ctgagccaat tcatggacca gaacaacccg ctg          113

<210> SEQ ID NO 51
<211> LENGTH: 72
<212> TYPE: DNA
<213> ORGANISM: Artificial
<220> FEATURE:
<223> OTHER INFORMATION: Synthetic

<400> SEQUENCE: 51
tcggggttga cccacaagcg ccgactgtcg gcgctggggc cggcggtct gtcacgtgag     60 cgtgccgggc tg                                                        72

<210> SEQ ID NO 52
<211> LENGTH: 115
<212> TYPE: DNA
<213> ORGANISM: Artificial
<220> FEATURE:
<223> OTHER INFORMATION: Synthetic

<400> SEQUENCE: 52
cgtggaggcg atcacaccgc agacgttgat caacatccgg ccggtggtcg ccgcgatcaa    60
ggagttcttc ggcaccagcc agctgagcca attcatggac cagaacaacc cgctg        115
```

```
<210> SEQ ID NO 53
<211> LENGTH: 78
<212> TYPE: DNA
<213> ORGANISM: Artificial
<220> FEATURE:
<223> OTHER INFORMATION: Synthetic

<400> SEQUENCE: 53
tcggggttga cccacaagcg ccgactgtcg gcgctggggc ccggcggtct gtcacgtgag     60
cgtgccgggc tggaggtc                                                  78
```